United States Patent
Dolle et al.

(10) Patent No.: US 10,668,102 B2
(45) Date of Patent: Jun. 2, 2020

(54) LINEAGE DIFFERENTIATION OF ENCAPSULATED EMBRYONIC STEM CELLS

(71) Applicant: Rutgers, The State University of New Jersey, New Brunswick, NJ (US)

(72) Inventors: Jean-Pierre Dolle, Metuchen, NJ (US); Rene S. Schloss, East Brunswick, NJ (US); Martin L. Yarmush, Newton, MA (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 85 days.

(21) Appl. No.: 15/298,827

(22) Filed: Oct. 20, 2016

(65) Prior Publication Data

US 2017/0100436 A1 Apr. 13, 2017

Related U.S. Application Data

(62) Division of application No. 13/151,912, filed on Jun. 2, 2011, now abandoned.

(Continued)

(51) Int. Cl.
*A61K 35/28* (2015.01)
*A61K 35/545* (2015.01)
(Continued)

(52) U.S. Cl.
CPC .......... *A61K 35/28* (2013.01); *A61K 9/4816* (2013.01); *A61K 35/545* (2013.01); *A61K 47/36* (2013.01);
(Continued)

(58) Field of Classification Search
None
See application file for complete search history.

(56) References Cited

U.S. PATENT DOCUMENTS 6,429,013 B1 8/2002 Halvorsen et al.
6,761,887 B1 7/2004 Kavalkovich et al.
(Continued)

FOREIGN PATENT DOCUMENTS

CA 2668200 A1 5/2008
WO 2006122147 A2 11/2006
(Continued)

OTHER PUBLICATIONS

Guan et al. "Embryonic stem cell-derived neurogenesis Retinoic acid induction and lineage selectin of neuronal cells" Cell Tissue Res (2001) 305: 171-176 (Year: 2001).*
(Continued)

*Primary Examiner* — Blaine Lankford
*Assistant Examiner* — Lauren K Van Buren
(74) *Attorney, Agent, or Firm* — Fox Rothschild LLP

(57) ABSTRACT

This application discloses alginate microencapsulation-mediated differentiation of embryonic stem cells and use of the stem cell differentiation method for the development of effective treatment of various diseases and disorders. The microencapsulation of embryonic stem (ES) cells results in decreased cell aggregation and enhanced neural lineage differentiation through incorporating the soluble inducer retinoic acid (RA) into the permeable microcapsule system. This differentiation process can be augmented by differentiation pathway regulators such as PPAR agonists.

11 Claims, 29 Drawing Sheets

3D Protocol

Related U.S. Application Data

(60) Provisional application No. 61/354,998, filed on Jun. 15, 2010, provisional application No. 61/350,760, filed on Jun. 2, 2010.

(51) Int. Cl.

| | | |
|---|---|---|
| *A61K 47/36* | (2006.01) | |
| *C12N 5/0735* | (2010.01) | |
| *C12N 5/079* | (2010.01) | |
| *C12N 11/10* | (2006.01) | |
| *C12N 5/0775* | (2010.01) | |
| *A61K 9/48* | (2006.01) | |
| *A61K 35/12* | (2015.01) | |

(52) U.S. Cl.
CPC ......... *C12N 5/0606* (2013.01); *C12N 5/0618* (2013.01); *C12N 5/0622* (2013.01); *C12N 5/0663* (2013.01); *C12N 11/10* (2013.01); *A61K 2035/122* (2013.01); *A61K 2035/124* (2013.01); *A61K 2035/128* (2013.01); *C12N 2501/58* (2013.01); *C12N 2501/60* (2013.01); *C12N 2506/02* (2013.01); *C12N 2533/74* (2013.01)

(56) References Cited

U.S. PATENT DOCUMENTS

| | | | |
|---|---|---|---|
| 7,015,037 B1 | 3/2006 | Furcht et al. | |
| 8,790,705 B2 | 7/2014 | Geigle et al. | |
| 2005/0239897 A1 | 10/2005 | Pittenger et al. | |
| 2007/0060626 A1* | 3/2007 | McGarry | C07D 417/12 514/364 |
| 2007/0099969 A1* | 5/2007 | Avery | C07D 277/34 514/369 |
| 2008/0038233 A1 | 2/2008 | Freemont et al. | |
| 2008/0103165 A1* | 5/2008 | Barlow | A61K 31/19 514/297 |
| 2008/0206343 A1 | 8/2008 | Edinger et al. | |
| 2008/0318882 A1 | 12/2008 | Wang et al. | |
| 2009/0093372 A1* | 4/2009 | Agulnick | C12N 5/0603 506/9 |
| 2010/0003751 A1* | 1/2010 | Revel | C12N 5/0619 435/368 |

FOREIGN PATENT DOCUMENTS

| | | | |
|---|---|---|---|
| WO | 2006122551 A2 | 11/2006 | |
| WO | WO-2006122147 A2 * | 11/2006 | ............ C12N 5/067 |
| WO | 2009007979 A2 | 1/2009 | |

OTHER PUBLICATIONS

Saluja et al. "PPAR gamma agonists stimulate oligodendrocyte differentiation in tissue culture" GLIA 33:191-204 (2001) (Year: 2001).*
Cimini et al. "Emerging Role of Peroxisome Proliferator-Activated Receptors (PPARs) in the Regulation of Neural Stem Cells Proliferation and Differentiation" Stem Cell Rev (2008) 4:293-303. (Year: 2008).*
Saluja et al. "PPAR delta Agonists Stimulate Oligodendrocyte Differentiation in Tissue Culture" Glia 33: 191-204 (Year: 2001).*
Bright et al. "PPAR Regulation of Inflammatory Signaling in CNS Diseases" PPAR Research, vol. 2008, 12 pages (Year: 2008).*
Barminko et al., "Encapsulated Mesenchymal Stromal Cells for in-vivo Transplantation," Biotechnol. Bioeng. (Nov. 2011): 108(11):2747-2758.
Jacklenec et al., Progress in the Tissue Engineering and Stem Cell Industry "Are we there yet?," Tissue Engineering: Par B (2012): 18(3):155-166.
Goren et al., "Encapsulated human mesenchymal stem cells: a unique hypoimmunogenic platform for long-term cellular therapy," The FASEB Journal (Jan. 2010); 24:22-31.
Ross et al., "Delivery of Recombinant Gene Products to the Central Nervous System with Nonautologous Cells in Alginate Microcapsules," Hman Gene Therapy (Jan. 1, 1999); 10:49-59.
Bethea et al., "Targeting the host inflammatory response in traumatic spnal cord injury," Current Opinion in Neurology (2002); 15:355-360.
Cao, "Human Umbilical cord mesenchymal stem cells and the treatment of spinal cord injury" Chinenes Medical Journal (2009); 122(2):225-231.
Li, "Culture of Neural Stem Cells in Calcium Alginate Beads," Biotechnology Prog. (2006); 22:1683-1689.
Xu et al., "Chondrogenic Differentiation of Human Mesenchymal Stem Cells in Three-Dimensional Alginate Gels," Tissue Engineering: Part 1 (Nov. 5, 2008); 14:667-680.
Ma et al., "Chondrogenesis of human mesenchymal stem cells encapsulated in aglinate beads," J. Biomed Mater Res. A. (Feb. 1, 2003); 64(2):273-281.
Central Nervous System by Antranik (2018); 9 pages.

* cited by examiner

2D Monolayer Protocol

3D Protocol

Day 30, Control

Day 30, PPAR Alpha

Day 30, PPAR Delta

Day 30, PPAR Gamma

Oil Red O staining

Alcian Blue Staining

21 days

Empty Capsules 1.7% Alginate 2.2% Alginate 2.5% Alginate 60 days

LINEAGE DIFFERENTIATION OF ENCAPSULATED EMBRYONIC STEM CELLS

CROSS-REFERENCE TO RELATED APPLICATIONS

This application is a divisional application of U.S. application Ser. No. 13/151,912 filed on Jun. 2, 2011, which claims priority under 35 U.S.C. § 119(e) to U.S. Provisional Patent Application Ser. Nos. 61/350,760, filed on Jun. 2, 2010, and 61/354,998, filed on Jun. 15, 2010, which are both hereby incorporated by reference in their entirety for all purposes.

FIELD OF THE INVENTION

The present invention relates to alginate microencapsulation-mediated differentiation of stem cells and use of the stem cell differentiation method for the development of effective treatment of various diseases or disorders. The invention also relates to a micro-encapsulation system for immobilizing stem cells, methods for delivery of encapsulated stem cells into the central nervous system, and use of the encapsulated stem cells as cellular transplantation therapies.

BACKGROUND OF THE INVENTION

Unlike adult differentiated tissue cells, pluripotent stem cells, such embryonic stem (ES) cells, can divide and self-renew indefinitely in-vitro and can also give rise to specialized cell types that can potentially form all tissues of the body (Evans, M. J. and Kaufman, M. H., *Nature,* 292(5819):154-156 (1981); Martin, G. R., *Proc. Natl. Acad. Sci. USA,* 78(12):7634-7648 (1981)). Therefore, the development of successful stem cell differentiation strategies to specific functional cell lineages offers the possibility of utilizing renewable cell sources to treat a large number of devastating conditions such as Parkinson's and Alzheimer's diseases, spinal cord injury, heart disease, diabetes, etc. (Cao, Q., et al., *J. Neurosci. Res.,* 68(5):501-510 (2002); Dinsmore, J., et al., *Cell Transplant.,* 5(2):131-143 (1996)). In addition to their applications in cell replacement, generation of mature cell types from stem cells could also provide materials for pharmacological and toxicological testing to improve the safety and efficacy of new drugs (O'Neill, A. and Schaffer, D. V., *Biotechnol. Appl. Biochem.,* 40(Pt 1):5-16 (2004)). However, the enormous potential of stem cells relies on the effective generation of large numbers of functionally stable and homogenous differentiated cell populations. Although many investigators have described techniques to successfully differentiate stem cells into different mature cell lineages using growth factors or extracellular matrix protein supplementation (Bain, G., et al., *Dev. Biol.,* 168(2):342-357 (1995); Kitazawa, A. and Shimizu, N., *J. Biosci. Bioeng.,* 100(1):94-99 (2005); Okabe, S., et al., *Mech. Dev.,* 59(1):89-102 (1996); Tian, H. B., et al., *Acta Biochim. Biophys. Sin.* (Shanghai), 37(7):480-487 (2005); Ying, Q. L., et al., *Nat. Biotechnol.,* 21(2):183-186 (2003)), most commonly in conjunction with embryoid body formation, improved control and scalability during the differentiation process can further enhance current methodologies. Therefore, in order to control differentiated cell output, a more complete understanding of the factors that regulate lineage commitment needs to be defined.

Mesenchymal stromal cells (MSCs) have shown therapeutic benefits in models of GVHD, myocardial infarction, fulminant hepatic failure, central nervous system trauma and others. MSCs reduce tissue inflammation in many traumatic or inflammatory disorders and thereby secondarily effect tissue repair. Researchers have suggested that MSCs, through soluble factor secretion instead of direct cell replacement, orchestrate cascades of biochemical cues which both mitigate fibrosis and promote tissue protection. These advances have propelled tissue protective MSCs to the forefront of cellular therapeutic development. An increasing interest has also been drawn to the capability of transplanted MSCs to improve SCI outcomes via secretion of cytokines and neurotrophic factors (Eaves, C. J., et al., *Blood,* 78, 110-117 (1991), Himes, B. T., et al., *Neurorehabil. Neural Repair,* 20, 278-296 (2006), Parekkadan, B., et al., *PLoS ONE,* 2, e941 (2007) et al.), which may both reduce inflammation and promote neural cell growth and differentiation. Spinal cord injury (SCI) involves a primary mechanical injury followed by a series of cellular and molecular secondary events resulting in progressive destruction of spinal cord tissue. Functional deficits following SCI result from damaged axons, loss of neurons and glia, and demyelination, whereas the inflammatory reaction contributes to marked apoptosis and scar tissue formation, thereby preventing axon extension and re-establishment of appropriate neuronal connections.

Alginate, a biocompatible copolymer of mannuronic and guluronic acid, has been used for many cell and tissue engineering applications, including, to mature hepatocyte function, to encapsulate embryoid bodies, to promote EB differentiation and to induce MSC differentiation (Magyar, J. P., et al., *Ann. NY Acad. Sci.,* 944, 135-143 (2001), Steinert, A., et al., *J. Orthop. Res.,* 21, 1090-1097 (2003), Sun, A. M., et al., *Appl. Biochem. Biotechnol.,* 10, 87-99 (1984)), or to direct embryonic stem cells towards hepatocyte lineage (Maguire, T., et al., *Biotechnol. Bioeng.,* 98, 631-644 (2007), Maguire, T., et al., *Biotechnol. Bioeng.,* 93, 581-591 (2006)). Although studies have indicated that the microenvironment as well as the developmental status of MSCs can alter neural stem cell inductive signals (Croft, A. P. and Przyborski, S. A., *Exp. Neurol.,* 216, 329-341 (2009)), MSC tissue persistence, potential MSC differentiation and/or MSC migration away from the injury site are very complex and present dynamic problems, which are difficult to resolve, control and quantify.

In particular, several drawbacks in current MSC implantation approaches limit safe and controlled clinical trial implementation. These include, 1) directly transplanted MSCs exposed to the complex injury environment may be adversely affected early in the treatment process, 2) MSCs may migrate to undesired tissue locations, and 3) MSCs may differentiate into undesired end stage cells. These issues severely limit the development of controlled feasibility studies and ultimately translatability of MSC treatments into clinical settings. Many experimental variables of MSC use have not been thoroughly evaluated including molecular mechanism(s) of anti-inflammatory MSC function. Furthermore, recent findings have identified donor specific phenotypic MSC differences, further necessitating controlled approaches for cell delivery. Therefore, engineered methods for controlled MSC delivery, without comprising their tissue protective properties, must be developed, and there remains a need in cell replacement therapies using renewable stem cell sources such as MSCs to treat a wide range of degenerative diseases.

Moreover, although studies have established techniques to successfully differentiate stem cells into different mature cell lineages using growth factors or extracellular matrix protein supplementation in both two and three-dimensional configurations, their practicality is limited by lack of control and low yields of differentiated cells. In particular, engineered methods for controlled MSC delivery, without compromising their tissue protective properties, must be developed, and there remains a need in cell replacement therapies using renewable stem cell sources, such as embryonic stem cells and MSCs, to treat degenerative diseases or disorders.

SUMMARY OF THE INVENTION

The present invention fulfills the present need. The present invention provides an alginate-based microencapsulation system to immobilize stem cells while inducing desired differentiation of the stem cells.

In one broad aspect the present invention provides a method for promoting differentiation of embryonic stem cells (ES cells) into neural lineage cells using an alginate-based microencapsulation system.

In another broad aspect the present disclosure provides a method for promoting differentiation of mesenchymal stromal cells (MSCs) into desired end stage cells using an alginate-based microencapsulation system for their use in cellular transplantation therapy.

Thus, in one aspect the present invention provides a method for inducing differentiation of stem cells into desired lineage cells, comprising: (a) encapsulating the stem cells within an alginate polyelectrolyte microenvironment; (b) culturing the encapsulated stem cells in a differentiation cell media; and (c) allowing the encapsulated stem cells to differentiate into the desired lineage cells or end stage cells optionally in the presence of an inducer capable of inhibiting cell aggregation. The stem cells can be either embryonic stem cells or mesenchymal stromal cells.

In another aspect the present invention provides an isolated cell population comprising a single-cell suspension of stem cells encapsulated within an alginate polyelectrolyte microenvironment, wherein the encapsulated ES cells are capable of differentiating within said microenvironment into desired lineage or end stage cells.

In one embodiment of this aspect, the invention provides an isolated cell population including a single-cell suspension of embryonic stem cells (ES cells) encapsulated within an alginate polyelectrolyte microenvironment, wherein the encapsulated ES cells are capable of differentiating within this microenvironment into neural lineage cells in the presence of retinoic acid supplementation.

In another embodiment of this aspect, the invention provides an isolated cell population including a single-cell suspension of mesenchymal stromal cells (MSCs) encapsulated within an alginate polyelectrolyte microenvironment, wherein the encapsulated ES cells are capable of differentiating within this microenvironment into desired end stage cells.

In another aspect the present invention provides a microencapsulation system comprising an alginate polyelectrolyte, wherein the system is capable of immobilizing mesenchymal stromal cells (MSCs) within an alginate microenvironment while sustaining molecular communication, wherein the encapsulated MSCs are capable of differentiating within said alginate microenvironment into desired end stage cells, and wherein said alginate microenvironment is capable of sustaining the MSC viability for a pre-determined amount of time.

In another aspect the present invention provides a method for promoting tissue repair or regeneration, or for treating spinal cord injury (SCI) or other inflammatory diseases or conditions in a subject, comprising administering to the subject an effective dose of MSCs encapsulated within an alginate polyelectrolyte microenvironment, wherein the encapsulated MSCs are capable of differentiating within said microenvironment into desired end stage cells.

In another aspect the present application discloses that by incorporating the soluble inducer, e.g., retinoic acid (RA), into the permeable microcapsule system, cell aggregation was decreased and neuronal lineage differentiation enhanced.

In another aspect the present invention provides that even in the absence of RA, differentiation could be directed away from the hepatocyte and towards the neural lineage by physical cell-cell aggregation blocking. In conjunction with the mechanical and physical characterization of the alginate crosslinking network, 2.2% alginate microencapsulation can be optimally adapted to ES neuronal differentiation. This aspect of the invention provides targeting cellular differentiation towards both endodermal and ectodermal cell lineages.

In another aspect the present invention provides a method for maintaining a neural cell differentiated state. The method includes culturing encapsulated single embryonic stem cells (ES cells) in differentiation cell media, wherein the encapsulated ES cells are encapsulated within an alginate polyelectrolyte microenvironment. The method also includes allowing the cultured encapsulated ES cells to differentiate into neural lineage cells in the presence of retinoic acid supplementation; and maintaining the differentiated state of the neural cells by maintaining the encapsulated differentiated cells in the differentiation cell media comprising retinoic acid.

In another aspect the present invention provides that differentiation approaches to efficiently generate large homogenous neural cell populations offer the potential to investigate and treat a variety of neurological disease processes mediated both by traumatic and naturally occurring events. The inventors have developed a method, using alginate microencapsulation, to generate all neuronal lineage cell types from stem cells. This process is scalable and may be used for both clinical treatment and drug discovery protocols. In addition, the differentiation process of the present invention can be augmented by culture supplementation of specific differentiation pathway regulators (e.g., PPAR agonists) which yield, for example, more than 80% myelin basic protein+ (protein positive) cells. Other pathways may also be targeted for cell specific enrichment.

In another aspect the present invention provides a kit. The kit includes single embryonic stem cells (ES cells) encapsulated within an alginate polyelectrolyte microenvironment, wherein the encapsulated single ES cells are capable of differentiating within this microenvironment into neural lineage cells in the presence of retinoic acid supplementation.

In another aspect the present invention encompasses new approaches within the microbeads to physically prevent cell aggregation, including but not limited to antibodies, and it could potentially include other physical structures either bound to cells or the alginate material.

In another aspect the present invention sought to determine if alginate encapsulated MSCs could attenuate inflammation and promote tissue repair. Through evaluation of an immobilization platform combining several different alginate concentrations and cell seeding densities, among others, the results indicate that this system can sustain MSC proliferation and viability for at least 3 months in vitro. In addition, depending on the alginate concentration, MSCs could either be maintained as undifferentiated cells (vital to sustaining tissue protective properties), or induced to differentiate into chondrocyte lineage cells. The data demonstrate that the microencapsulation platform can support constitutive MSC secretion patterns and that this function is also dependent upon alginate concentration. Furthermore, MSCs in the presence of pro-inflammatory stimuli, can be induced to secrete these factors at increased rates. Finally, via an in vitro model of macrophage inflammation attenuation, we have demonstrated that MSCs can mitigate inflammatory aspects of trauma mediated tissue damage by inducing a macrophage phenotype which promotes tissue remodeling rather than degeneration.

These and other aspects of the present invention will be better appreciated by reference to the following drawings and detailed description.

BRIEF DESCRIPTION OF THE DRAWINGS

FIG. 12A) Control Cells, i.e. untreated, FIG. 12B) Cells exposed to PPAR alpha agonist, FIG. 12C) Cells exposed to PPAR delta agonist, FIG. 12D) Cells exposed to PPAR gamma agonist.

FIG. 16A) MSC viability is dependent on initial cell seeding density, with cell seeding densities of 2 million-4 million being optimal; FIG.

16B) MSCs can remain viable in alginate capsules for at least 2 months post encapsulation; FIG. 16C) MSC proliferation is sustained in an alginate concentration of 2.2% and absent in concentrations of 1.7% and 2.5%.

DETAILED DESCRIPTION OF THE INVENTION

Figure 1:
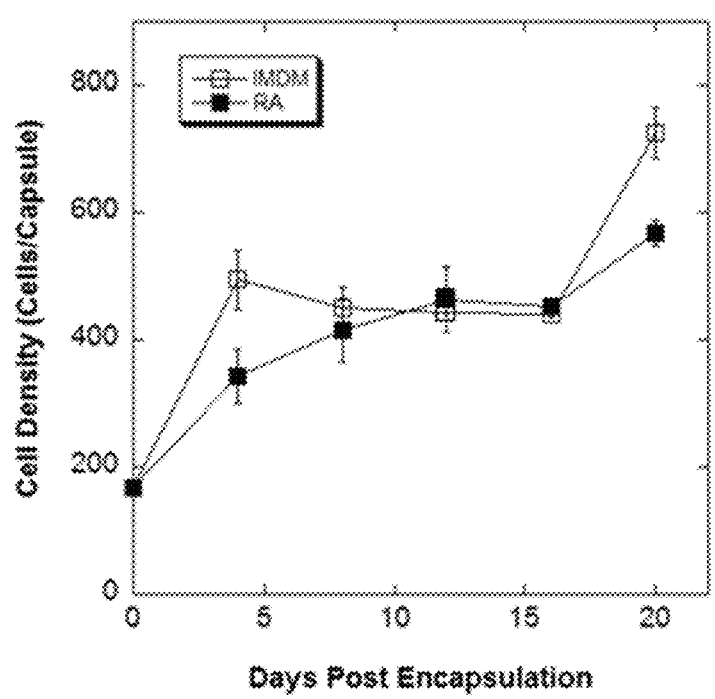
FIG. 1 illustrates the kinetic profile of cell density in alginate microencapsulation differentiation system. ES cells were encapsulated in 2.2% (w/v) alginate at a cell seeding density of $5 \times 10^6$ cells/ml, and cultured in IMDM with and without $10^{-7}$ M trans-retinoic acid supplementation. Error bar represents standard error of the mean.

The terms "differentiation" and "differentiate" or the like are known in the art. The meaning is intended to include the potential of any and all types of stem or progenitor cells to produce more specialized or mature or committed progeny cells.

The term "differentiation inhibitory factor" or the like refers to a substance which acts to maintain an undifferentiated phenotype of cells.

The term "differentiation cell media" refers to a cell media that promotes differentiation of cells (e.g., stimulates them to become committed to a desired cell lineage, such as a neural-lineage cell.

The term "embryoid body" or "embryoid bodies," as known in the art, refers to aggregate or aggregates of cells derived from embryonic stem cells. Upon aggregation, differentiation is initiated.

The term "growth factor," as used herein, refers to a substance that is involved in cell differentiation and growth. The term is meant to include any regulator substance in morphogenesis.

The term "inducer" or "differentiation inducer," as used herein, refers to a compound or agent that induces differentiation of stem cells into a desired functional cell lineage, for example, neural lineage.

The term "single-cell suspension," as used herein, refers to a suspension comprising cells that exist in non-aggregated forms.

Conventional molecular biological or cell biological techniques are disclosed, for example, in the following references: "Current Protocols in Molecular Biology" vols. I-III (F. Ausubel, Ed. 1994); "Cell Biology: a Laboratory Handbook" vols. I-III (J. E. Cellis, Ed. 1994); "Animal Cell Culture" (R. I. Freshney, Ed. 1986). The molecular biological and cell biological techniques disclosed in these references are incorporated herein by reference.

The present invention, in one aspect, sought to investigate the feasibility of using the scalable and controllable alginate microenvironment culture system to induce embryonic stem (ES) cells to differentiate into cells of other germ layer lineages, specifically neural lineage cells. Using the current approach, the inventors assessed whether, by incorporating soluble inducers and manipulating capsule parameters, they could differentially regulate and target cellular differentiation away from hepatocytes and towards distinct neuronal cell lineages. The results of these studies indicated that neural lineage commitment was based not only upon chemical and substrate based cues, but also on inhibition of intercellular aggregation within the alginate microbeads.

Thus, in one aspect the present invention provides a scalable and controllable alginate microenvironment culture system to induce ES cells to differentiate into cells of other germ layer lineages, e.g., in addition to hepatocyte, neural lineage cells. The invention provides incorporating soluble inducers and manipulating capsule parameters to regulate and target cellular differentiation away from hepatocytes and towards distinct neuronal cell lineages.

In this aspect the present invention provides a method for promoting differentiation of embryonic stem cells (ES cells) into functional neural cells. The method includes encapsulating a single-cell suspension of ES cells within an alginate polyelectrolyte microenvironment. The method also includes culturing the encapsulated cells in differentiation cell media; and allowing the encapsulated ES cells to differentiate into neural lineage cells in the presence of retinoic acid supplementation.

Specifically, the present invention provides a method for inducing differentiation of stem cells into desired lineage cells, comprising: (a) encapsulating the stem cells within an alginate polyelectrolyte microenvironment; (b) culturing the encapsulated stem cells in a differentiation cell media; and (c) allowing the encapsulated stem cells to differentiate into the desired lineage cells or end stage cells optionally in the presence of an inducer capable of inhibiting cell aggregation.

In one embodiment of this aspect, said encapsulating comprises: (i) dissolving an alginic acid salt in a medium to form an alginate solution; (ii) optionally filtering the alginate solution through a filter; (iii) adding to the alginate solution an aliquot of stem cell suspension to form a cell-alginate mixture; (iv) generating alginate beads using an electrostatic bead generator; (v) allowing the alginate beads to polymerize; and (vi) suspending the beads in a solution comprising a polyelectrolyte.

In another embodiment of this aspect, said culturing comprises: (i) removing the polyelectrolyte solution; (ii) washing the beads; (iii) suspending the washed beads in a differentiation media, wherein said differentiation media optionally comprises an inducer; and (iv) optionally replacing the differentiation media periodically.

In a preferred embodiment of this aspect, the stem cells are embryonic stem cells (ES cells).

In another preferred embodiment of this aspect, said polyelectrolyte is poly-L-lysine.

In another preferred embodiment of this aspect, said inducer is retinoic acid.

In another preferred embodiment of this aspect, said polyelectrolyte is poly-L-lysine, and said inducer is retinoic acid.

In another preferred embodiment of this aspect, the stem cells are embryonic stem cells (ES cells), and the desired lineage is neural lineage.

In another preferred embodiment of this aspect, said stem cells are embryonic stem cells (ES cells), said polyelectrolyte is poly-L-lysine, said inducer is retinoic acid (RA).

In another preferred embodiment of this aspect, the stem cells are mesenchymal stromal cells (MSCs).

In another embodiment of this aspect, the method further comprises augmenting the differentiation process by supplementing the cell culture with a specific differentiation pathway regulator.

In another embodiment of this aspect, said supplementing comprising adding the regulator into the differentiation media at a differentiation acceleration stage.

In a preferred embodiment of this aspect, said specific differentiation pathway regulator is a PPAR agonist.

In a more preferred embodiment of this aspect, said specific differentiation pathway regulator is selected from the group consisting of PPAR agonists α, δ, and γ, or a combination thereof.

In another preferred embodiment of this aspect, said stem cells are mesenchymal stromal cells (MSCs), and said desired end stage cells are cartilage or chondrocyte cells.

In another aspect the present invention provides an isolated cell population comprising a single-cell suspension of stem cells encapsulated within an alginate polyelectrolyte microenvironment, wherein the encapsulated ES cells are capable of differentiating within said microenvironment into desired lineage or end stage cells.

In a preferred embodiment of this aspect, the stem cells are embryonic stem cells (ES cells).

In another preferred embodiment of this aspect, the stem cells are embryonic stem cells (ES cells), and the desired cell lineage is neural lineage.

In another preferred embodiment of this aspect, the stem cells are embryonic stem cells (ES cells), the desired cell lineage is neural lineage, and the single-cell suspension further comprises an inducer.

In another preferred embodiment of this aspect, the inducer is retinoic acid, and the neural lineage cells have a reduced level of cell-cell aggregation in comparison with an isolated cell population in the absence of the alginate polyelectrolyte microenvironment and/or the inducer.

In another preferred embodiment of this aspect, the stem cells are mesenchymal stromal cells (MSCs).

In another preferred embodiment of this aspect, the stem cells are mesenchymal stromal cells (MSCs), and the desired cell lineage is cartilage or chondrocyte cell lineage.

In another aspect the present invention provides a microencapsulation system comprising an alginate polyelectrolyte, wherein the system is capable of immobilizing mesenchymal stromal cells (MSCs) within an alginate microenvironment while sustaining molecular communication, wherein the encapsulated MSCs are capable of differentiating within said alginate microenvironment into desired end stage cells, and wherein said alginate microenvironment is capable of sustaining the MSC viability for a pre-determined amount of time.

In a preferred embodiment of this aspect, the alginate polyelectrolyte has a concentration in the range from about 1.7% (w/v) to about 2.5% (w/v).

In a more preferred embodiment of this aspect, the alginate polyelectrolyte has a concentration of about 2.2% (w/v).

In another preferred embodiment of this aspect, the alginate polyelectrolyte is poly-L-lysine. In a more preferred embodiment, poly-L-lysine has a concentration in the range from about 1.7% (w/v) to about 2.5% (w/v). In a most preferred embodiment, poly-L-lysine has a concentration of about 2.2% (w/v).

In another aspect the present invention provides a method for promoting tissue repair or regeneration, or for treating spinal cord injury (SCI) or other inflammatory diseases or conditions in a subject, comprising administering to the subject an effective dose of MSCs encapsulated within an alginate polyelectrolyte microenvironment, wherein the encapsulated MSCs are capable of differentiating within said microenvironment into desired end stage cells.

In one embodiment of this aspect, the spinal cord injury is characterized by an inflammatory condition in a spinal cord site of contusion, and the method comprises delivering an effective dose of alginate encapsulated MSCs directly into cerebrospinal fluid of the spinal cord at the *cauda equina*.

In a preferred embodiment, the subject is a mammal.

In a more preferred embodiment, the subject is a human.

In another more preferred embodiment, the subject is a human and the MSCs are human MSCs (hMSCs).

In another aspect the present application discloses that by incorporating the soluble inducer, e.g., retinoic acid (RA), into the permeable microcapsule system, cell aggregation was decreased and neuronal lineage differentiation enhanced.

In another aspect the present invention provides that even in the absence of RA, differentiation could be directed away from the hepatocyte and towards the neural lineage by physical cell-cell aggregation blocking. In conjunction with the mechanical and physical characterization of the alginate crosslinking network, 2.2% alginate microencapsulation can be optimally adapted to ES neuronal differentiation. This aspect of the invention provides targeting cellular differentiation towards both endodermal and ectodermal cell lineages.

In another aspect the present invention provides a method for maintaining a neural cell differentiated state. The method includes culturing encapsulated single embryonic stem cells (ES cells) in differentiation cell media, wherein the encapsulated ES cells are encapsulated within an alginate polyelectrolyte microenvironment. The method also includes allowing the cultured encapsulated ES cells to differentiate into neural lineage cells in the presence of retinoic acid supplementation; and maintaining the differentiated state of the neural cells by maintaining the encapsulated differentiated cells in the differentiation cell media comprising retinoic acid.

In another aspect the present invention provides that differentiation approaches to efficiently generate large homogenous neural cell populations offer the potential to investigate and treat a variety of neurological disease processes mediated both by traumatic and naturally occurring events. The inventors have developed a method, using alginate microencapsulation, to generate all neuronal lineage cell types from stem cells. This process is scalable and may be used for both clinical treatment and drug discovery protocols.

In addition, the differentiation process of the present invention can be augmented by culture supplementation of specific differentiation pathway regulators (e.g., PPAR agonists) which yield, for example, more than 80% myelin basic protein+(protein positive) cells. Other pathways may also be targeted for cell specific enrichment.

In another aspect the present invention provides a kit. The kit includes single embryonic stem cells (ES cells) encapsulated within an alginate polyelectrolyte microenvironment, wherein the encapsulated single ES cells are capable of differentiating within this microenvironment into neural lineage cells in the presence of retinoic acid supplementation.

In another aspect the present invention encompasses new approaches within the microbeads to physically prevent cell aggregation, including but not limited to antibodies, and it could potentially include other physical structures either bound to cells or the alginate material.

In another aspect the present invention was designed to determine if alginate encapsulated MSCs could attenuate inflammation and promote tissue repair. Through evaluation of an immobilization platform combining several different alginate concentrations and cell seeding densities, among others, the results indicate that this system can sustain MSC proliferation and viability for at least 3 months in vitro. In addition, the inventors observed that depending on the alginate concentration, MSCs could either be maintained as undifferentiated cells (vital to sustaining tissue protective properties), or induced to differentiate into chondrocyte lineage cells. The data also demonstrate that the microencapsulation platform can support constitutive MSC secretion patterns and that this function is also dependent upon alginate concentration. Furthermore, MSCs in the presence of pro-inflammatory stimuli can be induced to secrete these factors at increased rates. Via an in vitro model of macrophage inflammation attenuation, the invention has demonstrated that MSCs can mitigate inflammatory aspects of trauma mediated tissue damage by inducing a macrophage phenotype which promotes tissue remodeling rather than degeneration.

Thus, in one embodiment the present disclosure provides a micro-encapsulation system comprising alginate polyelectrolyte, wherein the system is capable of immobilizing MSCs within an alginate microenvironment while sustaining molecular communication, wherein the encapsulated MSCs are capable of differentiating within said alginate microenvironment into desired end stage cells, and wherein said alginate microenvironment is capable of sustaining the MSC viability for at least three (3) months.

In another embodiment the present disclosure provides an isolated cell population comprising a single-cell suspension of MSCs encapsulated within an alginate polyelectrolyte microenvironment, wherein the encapsulated MSCs are capable of differentiating within said microenvironment into desired end stage cells, in particular chondrocyte cells.

In another embodiment the present disclosure provides a kit comprising a single-cell suspension of MSCs encapsulated within an alginate polyelectrolyte microenvironment, wherein the encapsulated MSCs are capable of differentiating within said microenvironment into desired end stage cells, in particular chondrocyte cells.

In another embodiment the present disclosure provides a method for promoting tissue regeneration comprising administering to a patient a therapeutically effective amount of MSCs encapsulated within an alginate polyelectrolyte microenvironment. The patient is preferably a mammal, more preferably a human. The MSCs are preferably human MSCs (hMSCs).

In another embodiment the present disclosure provides the use of MSCs encapsulated within an alginate polyelectrolyte microenvironment for a cellular transplantation therapy, wherein said alginate polyelectrolyte microenvironment is capable of sustaining the MSC viability for up to at least three (3) months, and wherein said MSCs are capable of secreting a growth factor for promoting cellular proliferation and protection.

In another embodiment the present disclosure provides methods for delivery of encapsulated MSCs into the central nervous system and therapies derived from the methods.

In another embodiment the present disclosure provides methods for treating spinal cord injury (SCI) of a subject, comprising administering to the subject an effective dose of alginate-encapsulated MSCs. The patient is preferably a mammal, more preferably a human. The MSCs are preferably human MSCs (hMSCs).

In a preferred embodiment the present disclosure provides a method for treating an inflammatory condition in a spinal cord site of contusion, comprising delivering an effective dose of alginate encapsulated MSCs directly into cerebrospinal fluid of the spinal cord at the *cauda equina*.

DISCUSSION

Micro-Encapsulated Differentiation of Embryonic Stem (ES) Cells

Stem cell proliferation and differentiation are governed by unique local microenvironments (Engler, A. J., et al., *Cell*, 126(4):677-689 (2006)). Certain aspects of the microenvironment, especially the biochemical and mechanical environments, play critical roles in determining the lineage commitment of ES cells (Engler, A. J., et al., *Cell* 126(4): 677-689 (2006); Li, L., et al., *Ann. Biomed. Eng.*, 36(5): 865-876 (2008); Philp, D., et al., *Stem Cells*, 23(2):288-296 (2005)). For example, Engler et al. determined that mesenchymal stem cells (MSCs) commit to lineage specificity with extreme sensitivity to substrate elasticity. More specifically, MSCs were neurogenic on a soft polyacrylamide substrate, which has an elastic modulus comparable to brain tissue, while on comparatively rigid substrates that mimic collagenous bone, they were osteogenic. More recently, Leipzig et al. demonstrated that, by culturing neural stem cells on methacrylamide chitosan biomaterial, the three major neural lineages, neurons, oligodendrocytes and astrocytes responded to distinct substrate-based differentiation cues (Leipzig, N. D. and Shoichet, M. S., *Biomaterials*, 30(36):6867-6878 (2009)). Jiang et al. also employed DNA crosslinked polymeric hydrogel to examine cellular responses of primary rat spinal cord neurons to substrate compliances and extracellular matrix coating (Jiang, F. X., et al., *Ann. Biomed. Eng.*, 36(9):1565-1579 (2008)). Therefore, identifying specific cues in the microenvironments could provide new tools with which to promote the differentiation of stem cells into large numbers of functionally stable cell lineages.

Here, the invention reveals the feasibility of using alginate microencapsulation to study the interaction among ES cells, their surrounding substrate network and ultimately differentiation pathway selection. This differentiation system can potentially incorporate numerous cell specific cues to study the interactions between cell-biochemical, cell-cell and cell matrix factors. The results indicate that by using the soluble differentiation inducer, retinoic acid, a person skilled in the art would be able to differentiate murine embryonic stem cells to express an array of neural specific markers. In addition, the results showed that retinoic acid mediated differentiation pathway selection may be modulated, at least in part, through cellular aggregation inhibition in the alginate microenvironment. By physically blocking aggregation, one could further enhance neural differentiation even in the absence of the inducer.

By taking advantage of the permeability of the alginate microcapsules, the present inventors demonstrated the expression of neural specific markers following incorporation of the soluble inducer, retinoic acid. Whereas, both neuronal and astrocyte differentiation were controllable by the alginate material properties, and could be optimized using 0.2% alginate, while oligodendrocyte differentiation could not be further optimized with the array of alginate conditions selected. However, the present inventors determined that cellular aggregation control could regulate the selection of differentiation pathways towards either neural or hepatocyte lineage cells in the alginate microbeads, and could in fact sustain the differentiation of all three neuronal lineages.

In the current study, the inventors found that encapsulated ES cells remained viable in the presence and absence of retinoic acid supplementation. Following an initial lag-phase, they ultimately reached a cell density 2.5 times greater than the initial one. However, the cell density in general was much lower in the encapsulation microenvironment as compared to the 2-D tissue culture treated plates. This was consistent with the present inventors' previous observations using unsupplemented alginate microbeads which induced hepatocyte lineage differentiation. Although encapsulated cells continued to divide at a similar rate throughout the entire 20 day culture period, ES cells cultured in the absence of retinoic acid did not express neural lineage markers. In the presence of RA, on the other hand, the present inventors achieved significant neural lineage differentiation, in numbers comparable to those in traditional EB mediated differentiation from mouse embryonic stem cell line (Bain, G., et al., *Dev. Biol.*, 168(2):342-357 (1995); Schuldiner, M., et al., *Brain Res.*, 913(2):201-205 (2001)). Therefore, the present invention has demonstrated that neuronal lineage differentiation can be achieved within the alginate microenvironment with efficiency comparable to traditional EB-mediated culture.

After assessing the neural specific markers in the 2.2% (w/v) condition, experiment was designed to determine the effects of various alginate concentrations on neural differentiation from ES cells. Alginate gels comprise blocks of co-polymers of 1,4-linked β-D-mannuronic acid (M) and α-L-guluronic acid (G). The crosslinking reaction is triggered when cations, such as $Ca^{2+}$, replace the hydrogen bonding in guluronate chain as more than one G-block region align side by side. Keeping the G/M ratio constant, the microcapsule properties can be controlled by varying the concentration, and therefore alter the polymer gel's stiffness. By comparing the percent of cells positively staining for neural specific markers, the present inventors found that 2.2% was most conducive to ES differentiation to astrocytes and neuronal lineage cells. Interestingly, this coincides with the condition that was found to be optimal for promoting hepatocyte differentiation in the alginate micro-beads. Oligodendrocyte differentiaton efficiency was not altered by varying the alginate properties.

A noteworthy observation is that, in the presence of retinoic acid, encapsulated cells showed markedly deceased cell aggregation and the size of individual cells was approximately 13 μm throughout the entire differentiation period. This cell size corresponds to the crosslinker spacing of 2.2% alginate gels, the optimal alginate concentration for differentiation induction for both neural and hepatocyte lineages (Maguire, T., et al., *Biotechnol. Bioeng.*, 93(3):581-591 (2006)). It is currently unclear whether physical structure contributes to metabolic transport, or other factors that may control differentiation within the microbeads. The data suggest that identical alginate properties can control differentiation toward both hepatocyte and neural lineages. Therefore alginate microbead design may serve to optimize differentiation induction in general, while aggregation control within the microbead may serve to direct lineage specificity.

After demonstrating neural differentiation within the alginate microcapsules induced by retinoic acid supplementation, the present inventors sought to investigate the mechanism of multi-lineage differentiation control in the encapsulation microenvironment. During basal media differentiation condition, hepatic function, such as intracellular albumin expression gradually increased during the 21 day incubation period in the encapsulation microenvironment. These studies also indicated that other hepatocyte functions, such as urea and albumin secretion, as well as increased expression of cytokeratin 18 and cyp 450 7A1, occurred concomitantly with the onset of cell aggregation. In addition, the expression of surface adhesion molecular E-Cadherin was greatly up-regulated, which also correlated with the onset of cell aggregation in the basal media condition (Maguire, T., et al., *Biotechnol. Bioeng.*, 98(3):631-644 (2007); Maguire, T., et al., *Biotechnol. Bioeng.*, 93(3): 581-591 (2006)).

However, while only a small portion of retinoic acid treated cells expressed E-Cadherin, the aggregate size was significantly decreased throughout culture period in the encapsulation microenvironment in the presence of retinoic acid. Although the effects of retinoic acid on embryonic stem cell aggregation are not fully understood, previous studies have demonstrated more than 75% decrease in aggregate volume of embryonal carcinoma cell P19 culture treated in retinoic acid as compared to the untreated case (Jones-Villeneuve, E. M., et al., *J. Cell Biol.*, 94(2):253-262 (1982); Jones-Villeneuve, E. M., et al., *Mol. Cell Biol.*, 3(12):2271-2279 (1983)). However the volume decrease only affected the cells in which neurons and glia were destined to develop. Retinoic acid-treated RAC65 cells, another embryonal carcinoma cell line that differentiates into fibroblast-like cells, did not show such a volume decrease. These results suggest the possibility that cell aggregation disruption might be associated with RA mediated neuronal progenitor cell commitment.

Based on the studies of cell aggregation and cell adhesion marker expression, the present inventors hypothesized that differentiation towards neural and hepatocyte lineage cells could possibly be modulated by controlling cell aggregation in the encapsulation microenvironment. Therefore an antibody blocking experiment, using anti-E-Cadherin antibody, was designed to prevent formation of cell aggregates. The experiment demonstrated that with continuous E-Cadherin blocking, hepatocyte functions diminished, while encapsulated cells increased neuronal marker expression and reached a plateau at the end of 24 day culture period. Although prevention of cell aggregation and concomitant neuronal differentiation can be achieved in the presence of the soluble inducer retinoic acid, the process cannot be sustained. Neural lineage markers decreased and albumin expression increased by day 12 post-differentiation induction and the re-emergence of the hepatocyte phenotype occurred concomitantly with cell re-aggregation. Based on the aggregation size study, once again small aggregates began to form after 12 days in the alginate microenvironment. To validate the aggregation-mediated hypothesis, the present inventors sought to further modulate cellular aggregation by increasing the concentration of blocking antibodies. These experiments demonstrated that increasing the blocking antibody concentration resulted in further inhibition of aggregate size during the 24 day differentiation period. In addition, expression of all three neural lineage specific markers gradually increased during the differentiation process.

In summary, in one broad aspect the present invention has demonstrated that alginate microencapsulation provides a potentially scalable system to control embryonic stem cell differentiation into neural lineage cells in the presence of a soluble inducer. As a result of the chemical inducer, capsule parameters and microenvironment manipulation, cellular differentiation can be directed to either hepatocyte or neuronal cell lineage. The invention has established a promising approach to modulate multiple lineage differentiation from renewable embryonic stem cells, in a mechanically defined culture environment. Ultimately cellular encapsulation of ES cells may provide a controllable approach to generate large numbers of differentiated cells for a variety of clinical and pharmaceutical applications.

Micro-Encapsulated Differentiation of Mesenchymal Stromal Cells (MSCs)

In addition to their differentiation potential, MSCs can promote tissue regeneration post organ trauma. Optimal regenerative MSC function may only be achieved if 1) an effective delivery vehicle is designed, 2) sustained regenerative secretion is established and 3) differentiation into unwanted lineages is controlled. The present inventors have developed an MSC alginate co-polymer micro-encapsulation approach that addresses each of these criteria and has the potential for in vivo implantation. This approach will provide a controllable method for culturing and implanting MSCs and has the potential for ultimate translation into the clinical milieu.

Thus, one objective of the present invention was to use alginate mesenchymal stromal cell encapsulation to (a) develop an immobilization platform for controlled delivery of anti-inflammatory mesenchymal stromal cells to areas of trauma, and (b) induce differentiation of MSCs into chondrocytes without differentiation factor supplementation. In order to circumvent various potential problems discussed above, this invention provides an alginate microencapsulation system as a vehicle for MSC delivery. Results show that MSCs proliferate and remain viable for at least 3 months post-encapsulation. Furthermore, in the absence of differentiation factor supplementation, the alginate microenvironment can be optimized to either prevent or promote differentiation of microencapsulated MSCs. While differentiated phenotypes were not detected post 2.2% (w/v) alginate encapsulation, MSCs encapsulated using 1.7% (w/v) alginate differentiated into chondrocyte lineage cells. In addition, our results indicate that the encapsulation platform 1) supports constitutive secretion of anti-inflammatory mediators, 2) augments the immune-suppressive MSC phenotype over time and 3) induces secretion of anti-inflammatory cytokines at increased rates upon induction with pro-inflammatory factors. Finally, using an in vitro model of macrophage activation, the invention has demonstrated that encapsulated MSCs can mitigate macrophage activation by attenuating the secretion of the pro-inflammatory factor, TNF-α. These studies provide that alginate micro-encapsulation can be used as cell-derived molecular delivery systems with sustained and long-term function for the treatment of various tissue pathologies.

MSCs can be used as a source of cell differentiation material and can induce other cells to differentiate. The encapsulated MSCs of the present invention possess both of these functions. The invention has demonstrated spontaneous differentiation into the chondrocyte lineage using 1.7% alginate, which is novel in that others have demonstrated this only after supplying differentiation factors. An important aspect of the present invention is that the alginate encapsulated MSCs of the present invention have tissue protective and anti-inflammatory properties, which are controlled via secreted products from the encapsulated MSCs and which may assist in reducing secondary consequences of traumatic injury or disease states. The capsules of the present invention are designed for in vivo injection for treatment of various conditions, including but not limited to nervous system trauma, arthritis, and other inflammatory disease states. The present invention has wide applications, including but not limited to 1) inducing differentiation into the cartilage cell lineage without the need for exogenous and expensive differentiation factors, and 2) inducing and controlling secretion of anti-inflammatory and regenerative mediators to attenuate inflammation and induce healing for a variety of in vivo applications, for both of which the present disclosure provides at least proof of concept.

The present disclosure also provides methods for the administration of MSCs into the central nervous system (CNS) of a human or animal patient and also to a method of treatment for spinal cord injury (SCI). The inventors have developed methods to deliver human MSCs encapsulated in alginate directly into the cerebrospinal fluid of spinal cord at the *cauda equina* in effective doses to reduce inflammatory responses at a distant spinal cord site of contusion at thoracic level 9-10 (T9-10). MSCs are known to exhibit anti-inflammatory responses when introduced to pro-inflammatory signals. However, direct contact between transplanted cells and the host may induce unfavorable immunological reactions that are diminished or eliminated by encapsulating MSCs and thereby preventing direct contact with the host. This also allows the use of non-autologous MSCs in a patient, and circumvents the delay required to collect and process autologous cells for individual patients. The pores in the alginate are sufficiently large to allow proteins and small molecules to pass between the encapsulated cells and host, thus allowing the transplanted MSCs to be activated by soluble pro-inflammatory signals and release anti-inflammatory molecules. All references cited are hereby incorporated by reference in their entireties herein.

The development of engineered systems for delivering MSCs to areas of organ trauma is vital for transition to a clinically relevant therapy. Unwanted migration and donor to donor variability will make clinical trials risky as well as difficult to control. Cell immobilization systems have long been proposed as a vehicle for delivering controlled release of therapeutic agents. However, to date no biological vehicle has been described that can maintain the secretion of the wealth of MSC therapeutic factors these cells provide, as well as circumvent fibrosis post encapsulation. Here cell immobilization was employed to determine if a system of encapsulated MSCs could be designed to create an implantable immune-modulatory bioreactor. Initial experiments were aimed at determining the optimal capsule parameters to sustain MSC viability. We determined that optimal cell seeding densities range from 2 to 4 million cells/ml. Concentrations of 1 and 6 million cells/ml resulted in viability decreases. At concentrations of 6 million cells/ml, limitations in oxygen and nutrient diffusion may have resulted, whereas at 1 million cells/ml critical cell to cell communication may have been sub-optimal, ultimately leading to increased cell death. Further, experiments may incorporate local oxygen depots which could potentially allow greater variation in seeding densities.

From evaluation of whether alginate immobilization can be used to provide a platform for long term MSC treatment, the inventors demonstrated sustained viability in alginate-encapsulated MSCs for at least 3 months in culture. Furthermore, depending on the concentration of alginate, the capsule microenvironment promoted MSC proliferation. These findings coincide with our previous observation that mouse embryonic stem cells can proliferate in 2.2% alginate but fail to do so in 1.7 or 2.5% alginate. The hypothesis that was proposed in those studies was that intra-capsular cross-linking in the 2.2% are optimal, providing appropriate diffusion and cell support.

The present invention was also designed to determine the optimal capsule parameters for maintaining the immature MSC phenotype. This process has been proposed to be controlled by the secretion and expression of several different factors in vitro and vivo, which may be altered once an MSC commits to a differentiated lineage. Therefore, capsules were assessed for markers representing differentiation into adipocyte, chondrocyte or osteocyte lineages following culture within beads composed of varying alginate concentrations. We were unable to detect osteocyte or adipocyte differentiation in any capsule configuration tested. However, chondrocyte differentiation was observed in capsules synthesized with 1.7% alginate. This differentiated phenotype was stable for at least 2 months. Several reports have described protocols for promoting MSC differentiation into chondrocytes within alginate capsules. However, in these reports differentiation could only be induced with cocktails of soluble factors.

MSCs have been found to mediate inflammation and promote tissue repair through the secretion of a variety of soluble mediators with a wide array of physiological effects. Therefore, the secretion profiles of encapsulated MSCs were evaluated to evaluate whether this characteristic was supported by the capsule platform. Evaluation of secretion from MSCs encapsulated in varying alginate concentrations revealed that depending on time in culture and alginate concentration, the secretion patterns can be controlled. On day 21, the secretion of different cytoprotective cytokines was elevated in the 2.2% condition and the secretory response was comparable to free MSCs. The mechanism by which MSCs control the inflammatory process is unclear, although it is suggested that in the presence of inflammatory factors, TNF-a and IFN-gamma the MSC anti-inflammatory phenotype is promoted (Ren, G., et al., Cell Stem Cell 2, 141-150 (2008)). The inventors here have studied this response using encapsulated MSCs.

The studies have demonstrated that encapsulated MSCs have the ability to mitigate the activation of M1 macrophages and that they can attenuate the secretion of TNF-a as well as IBA-1 expression. Furthermore, the percentage of cells positive for iNOS was determined to be lower in encapsulated MSC co-cultures. Interestingly, at this MSC to macrophage ratio, CD206, a marker for the M2 phenotype, was elevated. This data suggests that encapsulated MSCs may shift macrophages to the M2 phenotype. This is consistent with previous reports that MSCs promote the M2 phenotype in activated macrophage cultures (Kim, J. and Hematti, P., *Exp. Hematol.*, 2009. 37(12), 1445-1453 (2009)). Interestingly, the data suggests that in the capsule micro-environment, lower MSC cell numbers are needed to effect this transition. This may suggest that fewer MSCs may be needed to achieve therapeutic benefits in vivo as well. Ratios of M1 to M2 macrophages are emerging as a critical factor in determining tissue preservation or degradation (Kigerl, K. A., et al., *J. Neurosci.*, 2009. 29(43), 13435-13444 (2009)). MSC promoting the M2 phenotype may provide an environment suitable for tissue preservation and/or regeneration. Multiplex analysis revealed that encapsulated MSCs mitigate the secretion of several pro-inflammatory factors to levels comparable to non-activated macrophages. Several of these factors (MW-1a, MIP-1b and IL-8) have been found to be elevated early in tissue pathologies and are associated with facilitating tissue fibrosis (Tsai, M. C., et al., *Surg. Neurol.*, 2008, 70 Suppl. 1, S1:19-24 (2008)). Simultaneously, elevation in growth factor levels associated with tissue regeneration was observed in the encapsulated MSC conditions.

Overall the data here support the fact that encapsulated MSCs may be used as immune-modulatory bio-reactors in vivo. Alginate parameters were identified to maximize survival and MSC protein secretion. In addition, we demonstrated that encapsulated MSCs can contribute to the attenuation of macrophage activation in vitro. Additionally, the encapsulated MSCs were able to modulate macrophage function to a state which, in vivo, could promote tissue regeneration. The immobilization system developed here should circumvent many of the drawbacks in current MSC administration platforms and at the same time may serve to augment MSC tissue protective behavior.

Figure 23:
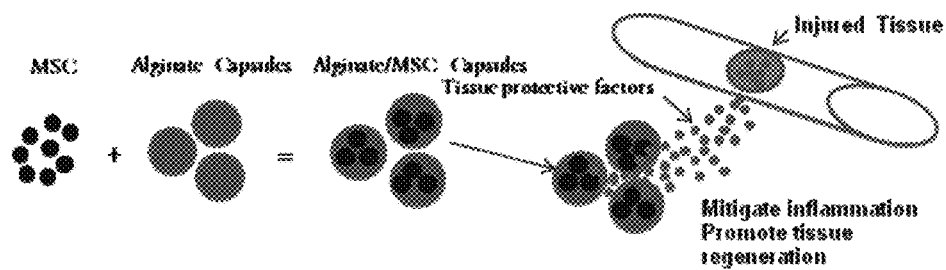
FIG. 23 illustrates the formation of alginate encapsulated MSCs and use of them to induce a macrophage phenotype that promotes post trauma tissue remodeling.

Thus, this invention proves, inter alia: 1) the alginate microenvironment can support MSC survival for as long as 3 months post encapsulation; 2) the alginate microenvironment can be optimized to provide platforms to both differentiate MSCs and/or sustain their immature phenotype, depending on the alginate concentration used; 3) within the alginate micro-capsule, MSCs secrete anti-inflammatory mediators, and encapsulated MSCs respond to pro-inflammatory stimuli by secreting anti-inflammatory factors at increased rates; 4) inflammatory tissue degrading macrophages can be attenuated in vitro by MSCs; and 5) encapsulated MSCs simultaneously induce a macrophage phenotype that promotes post trauma tissue remodeling (FIG. 23).

The present invention is described more fully by way of the following non-limiting examples.

EXAMPLES

Example 1

ES Cell Culture

All cell cultures were incubated in a humidified 37° C., 5% $CO_2$ environment. The ES cell line D3 (ATCC, Manassas, Va.) was maintained in an undifferentiated state in T-75 gelatin-coated flasks (Biocoat, BD-Biosciences, Bedford, Mass.) in Knockout Dulbecco's modified Eagles medium (Gibco, Grand Island, N.Y.) containing 15% knockout serum (Gibco), 4 mM L-glutamine (Gibco), 100 U/ml penicillin (Gibco), 100 U/ml streptomycin (Gibco), 10 mg/ml gentamicin (Gibco), 1,000 U/ml ESGRO™ (Chemicon, Temecula, Calif.) and 0.1 mM 2-mercaptoethanol (Sigma-Aldrich, St. Louis, Mo.). Media was changed every two days until plates were confluent. ES cultures were split and passaged every 6 days. Following media aspiration, cells were washed with 10 mL of phosphate buffered solution (PBS) (Gibco), detached using 3 mL of trypsin EDTA (Gibco) for 3 minutes, and subsequently 12 mL of Knockout DMEM was added. Cells were then replated in gelatin-coated T-75 flasks at a density of 1 million cells/mL and only passages 10 through 25 were used in the experiments. In order to induce differentiation, cells were cultured in Iscove's modified Dulbecco's medium (Gibco) containing 20% fetal bovine serum (Gibco), 4 mM L-glutamine (Gibco), 100 U/ml penicillin (Gibco), 100 U/ml streptomycin (Gibco), 10 mg/ml gentamicin (Gibco) in the presence or absence of $10^{-7}$M trans-retinoic acid (Sigma-Aldrich).

Example 2

Alginate Encapsulation

Alginate solution was prepared by dissolving 2.2 g of alginic acid sodium salt (MW: 100,000-200,000 g/mol, G Content: 65%-70%, Sigma-Aldrich) in 100 mL of $Ca^{2+}$ free DMEM (Gibco), using a heated magnetic stir plate at a temperature of 65° C. The solution was then filtered using a 45 µm syringe filter (Fisher Scientific, Pittsburgh, Pa.). To create the cell-alginate mixture, 1 mL aliquot of cell suspension with a seeding density of $5 \times 10^7$ cells/mL was added to 9 mL of either 1.2%, 1.7%, 2.2% or 2.5% (w/v) alginate solution to yield a final cell seeding density of $5 \times 10^6$ cells/mL. This solution was transferred to a 10 mL syringe, and was connected to a syringe pump (KD Scientific, MA). Alginate beads were generated using an electrostatic bead generator (Nisco, Zurich, Switzerland) at a flow rate of 40 mL/h, and an applied voltage of 6.4 kV. The beads were extruded into a 200 mL bath of $CaCl_2$ (100 mM), containing 145 mM NaCl, and 10 mM MOPS (all from Sigma-Aldrich) and were left to polymerize for 10 min at room temperature (Maguire, T., et al., *Biotechnol. Bioeng.*, 93(3):581-591 (2006)). Beads were then transferred to a tissue culture treated T-25 flask. The $CaCl_2$ solution was removed using a 5 mL pipette, and the beads were washed with 5 mL of HEPES (Gibco). The HEPES was removed and the beads were resuspended in 5 mL of poly-L-lysine (PLL) (Sigma-Aldrich, MW 68,600 g/mol) (0.05% w/v) for 2 min. The PLL was then gently removed, replaced with HEPES to wash the beads and the beads were ultimately resuspended into 5 mL of IMDM medium (Invitrogen, Carlsbad, Calif.) media with and without $10^{-7}$M trans-retinoic acid (Bain, G., et al., *Dev. Biol.*, 168(2):342-357 (1995)). Media was changed at days 4, 8, 12, 16 and 20 post-encapsulation.

Example 3

Assessment of Cell Proliferation and Neural Specific Protein Expressions

Under an optimized encapsulation condition (i.e. 2.2% w/v alginate and $5 \times 10^6$ cells/mL), experiments were designed to assess cell proliferation and the expression of an array of neural special markers during a 20-day differentiation period. Encapsulated cells were cultured in the presence or absence of RA, recovered on days 4, 8, 12, 16 and 20 post encapsulation by depolymerizating the alginate microcapsules, and cell number and viability were determined. As indicated in FIG. 1, encapsulated cell numbers in the presence or absence of retinoic acid were similar. The cell proliferation in both conditions exhibited biphasic kinetic properties, and the cultures ultimately reached a final density 2.5 times greater than the initial seeding density. Cell viability was greater than 95% in both conditions and throughout the culture period.

Figure 2:
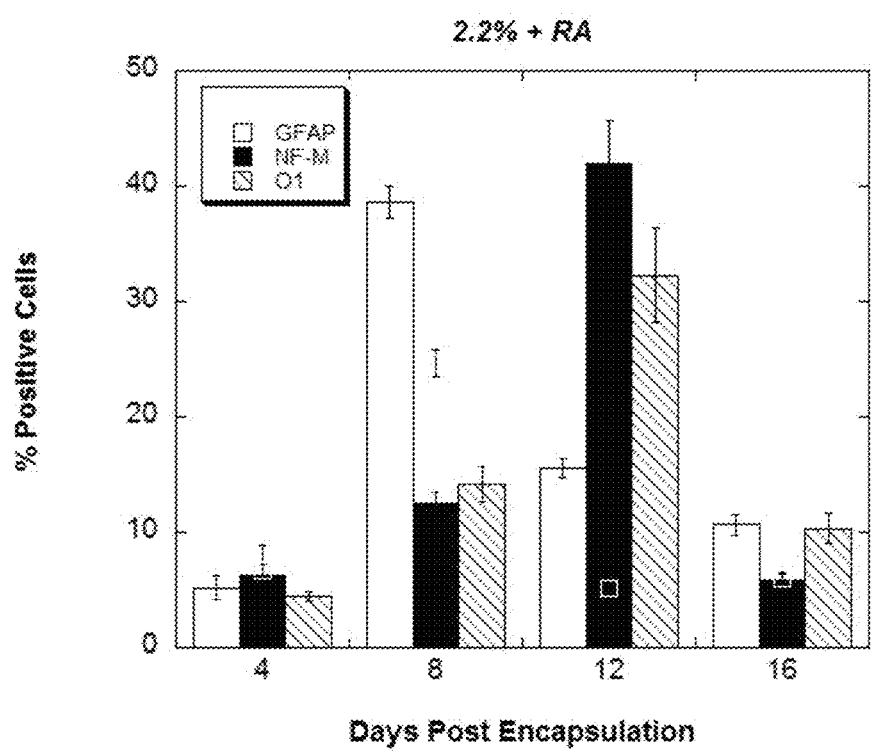
FIG. 2 illustrates the kinetic profile of percent of positive population in 2.2% alginate microencapsulation differentiation system in the presence of retinoic acid. ES cells were encapsulated at a cell seeding density of $5 \times 10^6$ cells/ml, and cultured in IMDM with $10^{-7}$ M trans-retinoic acid supplementation for 16 days. Error bar represents standard error of the mean.

To assess the effect of RA on lineage commitment within the alginate microenvironment, individual cells were examined within the encapsulated population using indirect immunofluorescence analysis with a panel of neural lineage specific antibodies, including neurofilament 160 kD (neuronal marker), O1 (oligodendrocyte marker) and GFAP (astrocyte marker). Specific antibody binding was assessed relative to a non-specific immunoglobulin control. The results of these experiments indicate that expression of all neural markers examined reached their maximal levels by Day 12. However, neural marker expression decreased dramatically by the end of the differentiation period as shown in FIG. 2. The maximum percentage of encapsulated cells positively stained for NF 150 kD, O1 and GFAP markers were 41.9%, 32.3% and 38.6% respectively following incubation in the presence of $10^{-7}$M retinoic acid. In contrast, less than 5% of encapsulated cells stained positively for intracellular albumin, a hepatocyte lineage cell marker. However, in the absence of any induction factor (i.e., under basal condition), while hepatocyte differentiation was favored with over 90% cells expressing intracellular albumin, only a very small fraction (<5%) of the encapsulated cells expressed the markers listed above.

After assessing the neural specific markers, the inventors also investigated the effects of different alginate concentrations, e.g., 1.2%, 1.7% and 2.5%, on neural differentiation in the alginate encapsulation microenvironment. The percent of cells which stained positively for neural specific markers is summarized in Table 1. These experiments indicated 2.2% was the most favorable condition for both astrocyte and neuronal lineage differentiation. However, alginate concentration changes had very little effect on oligodendrocyte differentiation efficiency.

TABLE 1

Comparison of Percent Positive Cells with and without Retinoic Acid Supplementation*

| Neural Specific Markers | O1 Oligo-dendrocyte Marker | NF-M Neuronal Marker | GFAP Astrocyte Marker | Albumin Hepatocyte Marker |
|---|---|---|---|---|
| Basal | <5% | <5% | <5% | >85% |
| 1.2% + RA | 30.6 ± 5.5% | 27.5 ± 4.2% | 18.1 ± 2.1% | 11.35 ± 0.35% |
| 1.7% + RA | 26.7 ± 4.1% | 24.5 ± 3.8% | 15.6 ± 0.8% | 17.74 ± 1.46% |
| 2.2% + RA | 32.3 ± 1.0% | 41.9 ± 2.6% | 38.6 ± 1.9% | 14.13 ± 0.85% |
| 2.5% + RA | 28.6 ± 2.7% | 33.7 ± 3.2% | 25.3 ± 1.9% | 15.11 ± 2.68% |

*The experiment was done in triplicate. Error bars represent standard error of the mean.

Example 4

Figure 3:
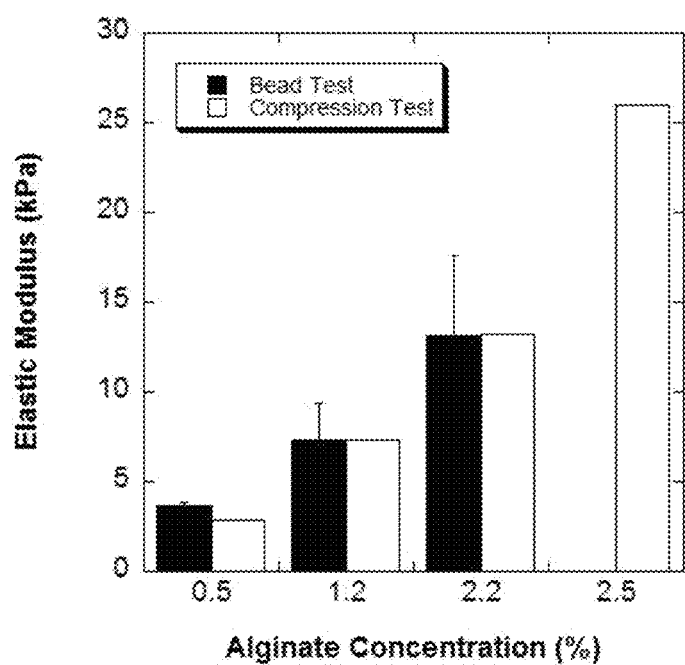
FIG. 3 illustrates the characterizations of mechanical properties of alginate gels at various concentrations. Variation of elastic modulus (using magnetic bead method) and compressive modulus (using compression method) of alginate gels with alginate concentration.

Assessment of Mechanical Properties and Crosslinking Density in Alginate Microcapsules In order to probe the three dimensional alginate microenvironment and the mechanical cues underlying the differentiation process, the present inventors examined the physical properties of alginate microcapsules at varying alginate concentrations. Both the bead test (for local mechanical property assessment) and compression test (for bulk mechanical property assessment) were adapted to determine the rigidity of the alginate microcapsules. The mechanical properties of the alginate microbeads were initially characterized using 1/16" spherical magnetic beads (see, Li, L., et al., *Ann. Biomed. Eng.*, 36(5):865-876 (2008)). Variation of alginate concentration produced microbeads with stiffnesses of 3.70, 7.35 and 13.13 kPa for 0.5%, 1.1% and 2.2% alginate concentrations respectively (FIG. 3). This method was sufficient for alginate gels up to 2.2% w/v. As the concentration of alginate monomer (with constant G/M ratio) continued to increase, the maximum magnetic force the present inventors applied was not big enough to cause displacement of the 1/16" steel ball. Therefore, the stiffness of 2.5% alginate gels was evaluated by standard tensile tests. As shown in FIG. 3, the elastic modulus determined by both compression and bead tests showed a clear dependence on alginate concentration. Furthermore, the moduli were consistent in both tests, suggesting relative homogeneity of the alginate encapsulation microenvironment.

Figure 4:
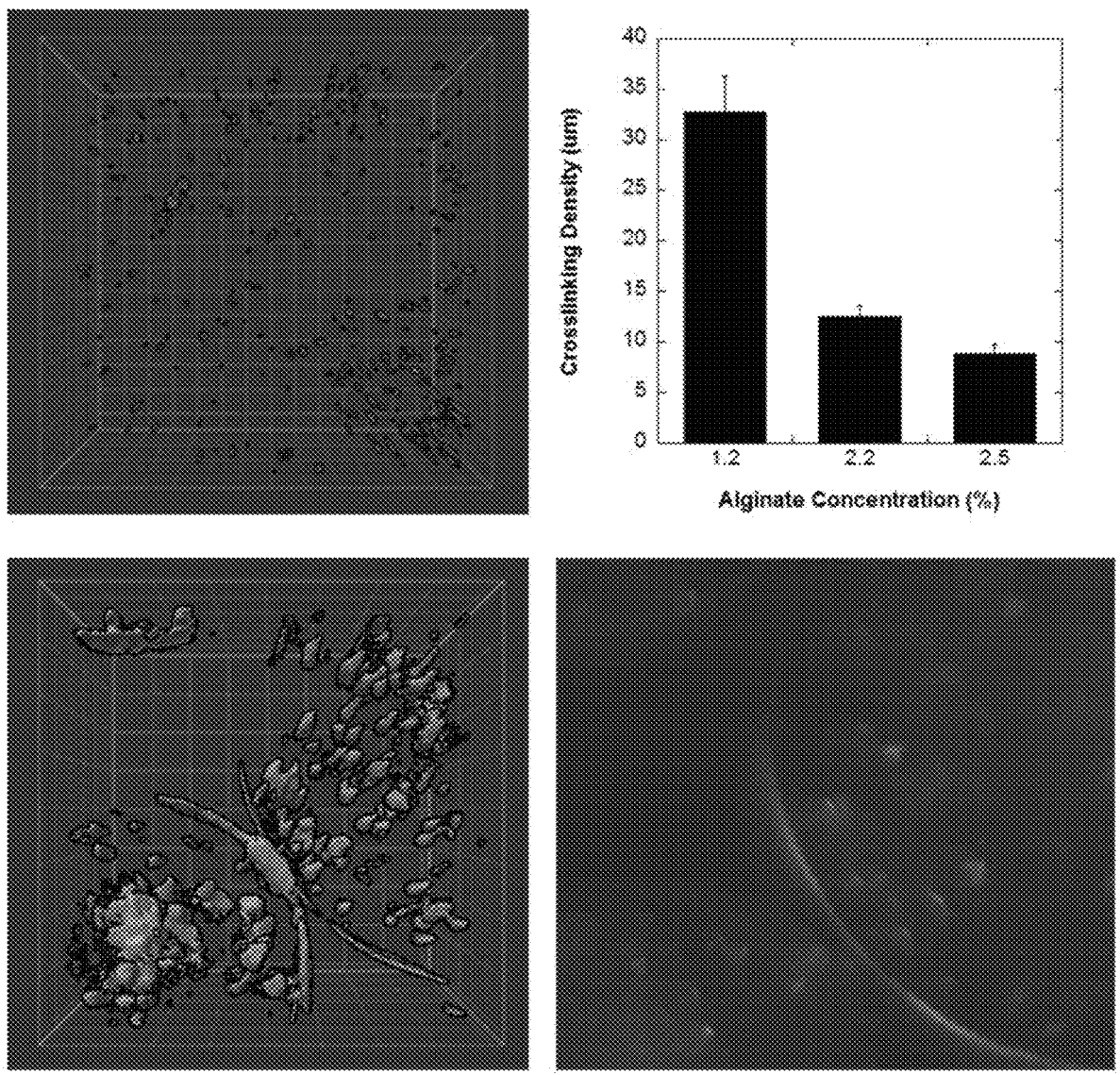
FIG. 4 illustrates the characterization of crosslinking density of alginate gels at various concentrations. (Top, Left) Representative 3D surface view of alcian blue staining of 2.2% empty capsules at 40× magnification based on stack images of 20 at 5 μm step size; (Top, Right) Variation of crosslinking spacing with alginate concentrations. The experiment was done in triplicate, with sample size of at least 5 beads per experiment. Error bars represent standard error of the mean. (Bottom, Left and Right) Representative 3D surface view and bright-field images of 2.2% alginate microbeads encapsulated with undifferentiated ES cells, where alcian blue stains both alginate crosslinking strands and glycoproteins on cells.

In addition to the rigidity of alginate crosslinking strands, the spacing between crosslinkers in the gel network was characterized using the alcian blue dye, since material compliance is mediated both by the chemical properties of the polymer strands (i.e. compliance of each strand) as well as physical association between the strands (i.e. the number of strands within a given polymer area or volume). A positively charged alcian blue dye was used because its molecular properties promote binding to the anionic carboxyl and half-ester sulfate groups of polysaccharide chains of alginate crosslinking strands (Powell, K. R., et al., *Anal. Biochem.*, 119(1):31-37 (1982)). From the 3-D surface view generated based on stacks of bright field images of the microcapsules, it was found that the alcian blue dye was aligned in one direction. Representative images empty capsules and capsules encapsulated with ES cells (A and C) and their corresponding 3-D surface view images are shown in FIG. 4. When the present inventors measured the spacing between crosslinkers in the alginate gel network, values of 8.8, 12.5 and 32.8 μm were measured for 1.2%, 2.2% and 2.5% microbeads respectively as shown in FIG. 4. These studies indicated that differentiation toward both neuronal and astrocyte lineages was optimal when alginate stiffness was set at about 13 kPa with an interstrand spacing of about 12 microns.

Example 5

Assessment of Cellular Aggregation During Neural Lineage Differentiation

The mechanical characterization studies suggested that initial differentiation cues to both neurons and astrocytes were at least partially controlled by material properties, but that oligodendrocyte differentiation was less controllable using the alginate bead configurations described above. Nevertheless, while all three lineages were induced by day 12, differentiation was not sustained, and was dramatically reduced by day 16. Based on our discovery that differentiation of hepatocyte lineage cells within the alginate microbeads may be correlated with formation of small cell aggregates, we also assessed the role of intracapsular cellular aggregation during neural lineage differentiation. In the presence of retinoic acid supplementation, encapsulated cells showed markedly decreased cell aggregation (FIG. 5) relative to non-supplemented cells. In fact, in the presence of retinoic acid, encapsulated cells remained as single cells throughout the 20 days culture period. In contrast, differentiating cells cultured in the basal media configuration continued to aggregate.

Since hepatocyte differentiation and E-Cadherin expression (a molecule known to regulate cell-cell contact) may occur concomitantly with hepatocyte functional responses (Maguire, T., et al., *Biotechnol. Bioeng.*, 98(3):631-644 (2007); Maguire, T., et al., *Biotechnol. Bioeng.*, 93(3):581-591 (2006)), the present inventors probed RA mediated effects on E-Cadherin expression during neural differentiation. The results indicated that the percentage of RA supplemented encapsulated cells expressing E-Cadherin was much lower compared to the cells differentiated in the basal condition. However, there was a significant re-expression of E-Cadherin on days 12 and 20 post differentiation induction, coinciding with a shift from neuronal towards hepatocyte phenotypes.

Example 6

Control of Cellular Differentiation by Antibody Blocking

Figure 5:
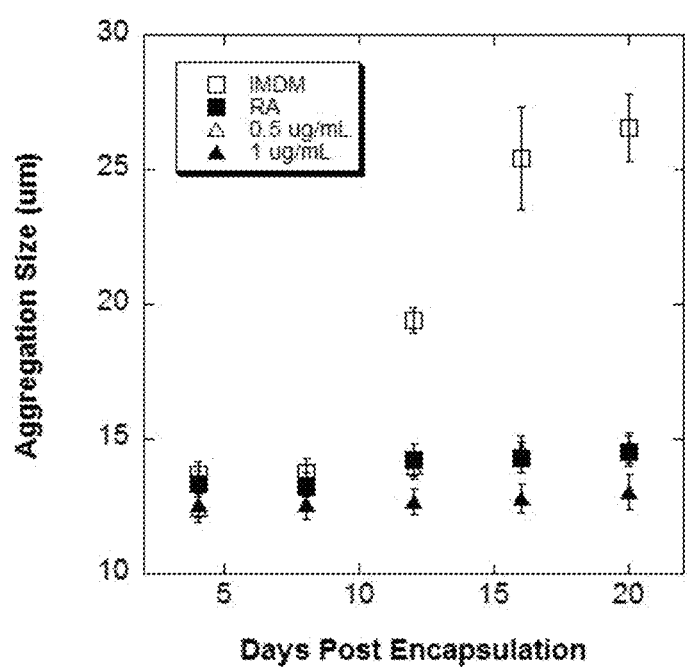
FIG. 5 illustrates the kinetic profile of size of aggregate formation in the alginate microencapsulation differentiation system. Time course of cell aggregate diameter. ES cells were encapsulated in 2.2% (w/v) alginate at a cell seeding density of $5 \times 10^6$ cells/ml, and cultured in IMDM with and without $10^{-7}$ M trans-retinoic acid supplementation, or with 0.5 and 1 μg/mL E-Cadherin antibody blocking. Error bars represent standard error of the mean.
Figure 6:
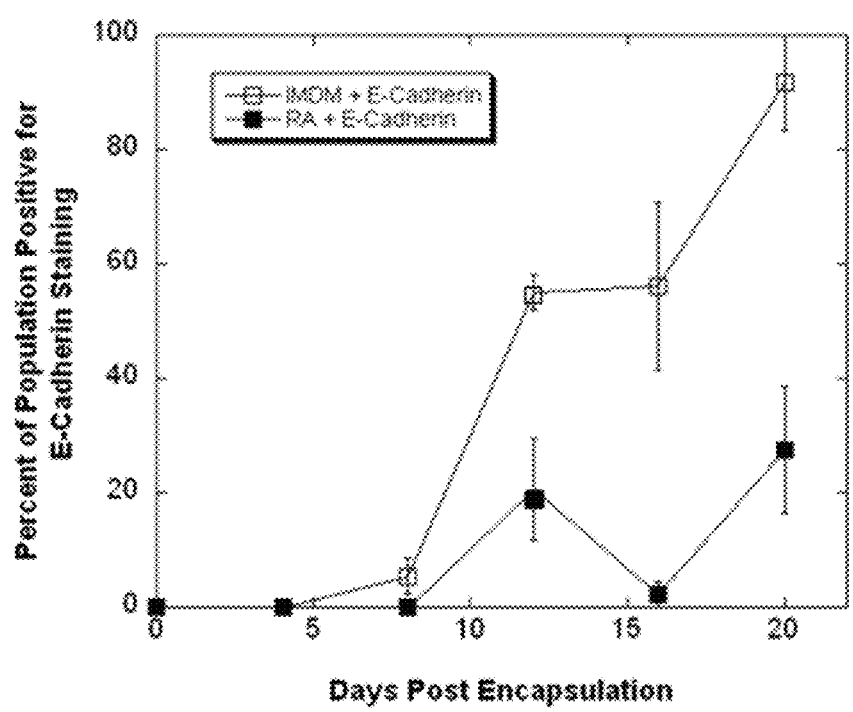
FIG. 6 illustrates expression of E-Cadherin in alginate microencapsulation differentiation system. Time course of percentage of encapsulated cells expressing cell adhesion molecule E-Cadherin. ES cells were encapsulated in 2.2% (w/v) alginate at a cell seeding density of $5 \times 10^6$ cells/ml, and cultured in IMDM with and without $10^{-7}$ M trans-retinoic acid supplementation. E-Cadherin intensity values were determined using intracapsular immunofluorescence staining and percent positive cells calculated. Error bars represent standard error of the mean.

Based upon the cell aggregation and E-Cadherin studies, the present inventors hypothesized that differentiation towards neural lineage cells could possibly be modulated by controlling cell aggregation in the encapsulation microenvironment even in the absence of retinoic acid. To prevent the formation of aggregates, 0.5 μg/mL of E-Cadherin and corresponding isotype antibodies were added to cultures (Maguire, T., et al., *Biotechnol. Bioeng.*, 98(3):631-644 (2007)). The net expression of neural specific markers was quantified by subtracting non-specific isotype antibody yields from cultures continuously exposed to E-Cadherin antibody blocking. As shown in FIG. 5, cell aggregate size was significantly reduced following E-Cadherin blocking. Furthermore, by blocking the cell aggregation using 0.5 mg/mL anti-E-Cadherin antibody, intracellular albumin expression declined dramatically, while encapsulated cells continued to express all three neuronal markers, NF 150 kD, O1 and GFAP marker at a later stage of the encapsulation even in the absence of retinoic acid in FIG. 7. Encapsulated cell sub-populations expressing neural specific markers, after reaching the maximum levels at Day 16 (Day 12 for neurofilament), plateaued by the end of the 24-day culture period in the presence of E-Cadherin blocking antibody.

Figure 7A:
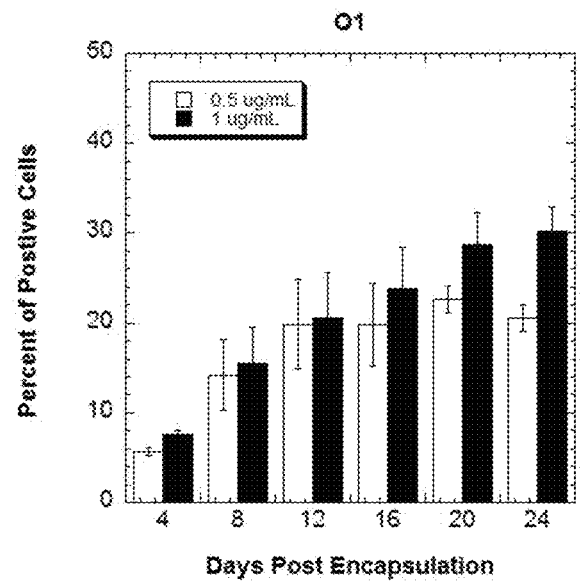
FIGS. 7A, 7B and 7C illustrate the kinetic profile of percent of positive population with E-Cadherin antibody blocking in alginate microencapsulation differentiation system. Time course of percentage of encapsulated cells expressing neurofilment 160 kD, O1, GFAP antibodies and intracellular albumin. ES cells were encapsulated in 2.2% (w/v) alginate at a cell seeding density of 5×106 cells/ml, and cultured in IMDM medium with 0.5 and 1 μg/mL of E-Cadherin antibody blocking. Fluorescent intensity values were determined using intracapsular immunofluorescence staining and percent positive cells calculated. Error bars represent standard error of the mean.
Figure 7B:
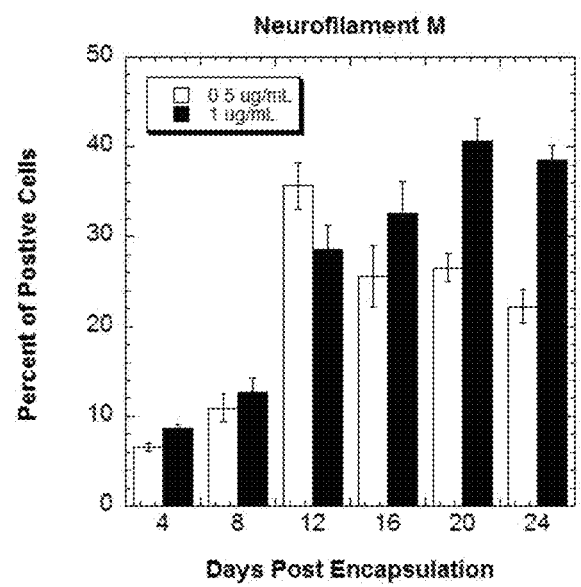
Figure 7C:
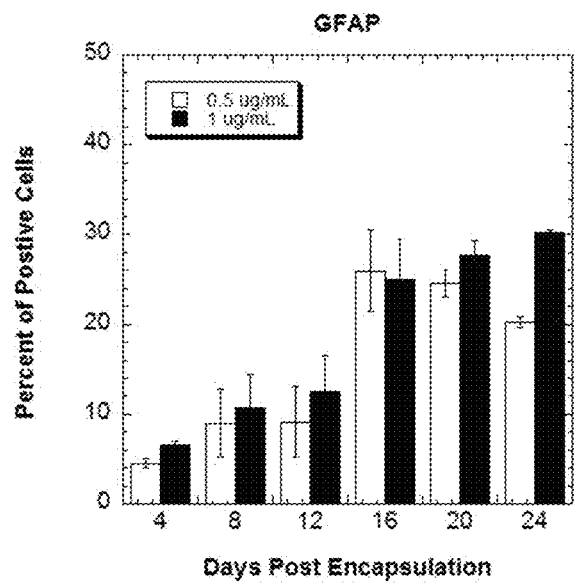
Figure 8:
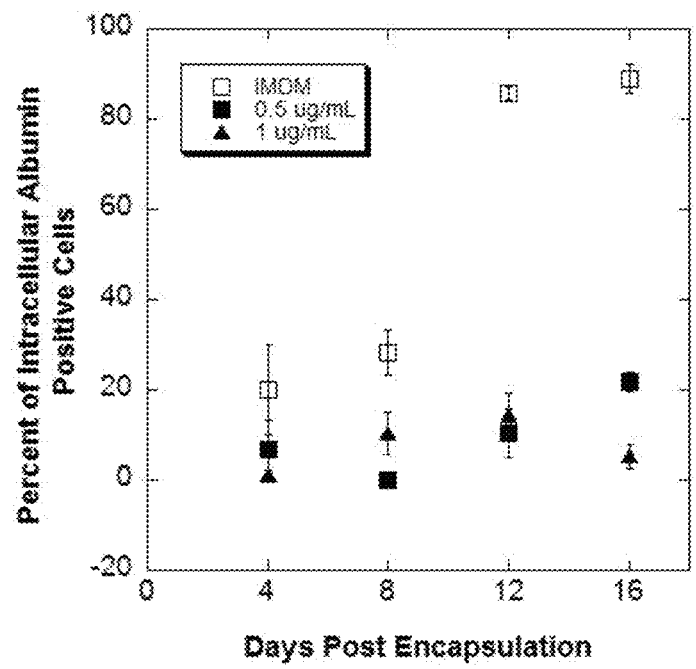
FIG. 8 illustrates the kinetic profile of percent of positive population of intracellular albumin expression with E-Cadherin antibody blocking in the alginate microencapsulation differentiation system. ES cells were encapsulated in 2.2% (w/v) alginate at a cell seeding density of 5×106 cells/ml, and cultured in IMDM medium alone and with 0.5 and 1 μg/mL of E-Cadherin antibody blocking. Fluorescent intensity values were determined using intracapsular immunofluorescence staining and percent positive cells calculated. Error bars represent standard error of the mean.

To further the analysis of E-Cadherin blocking for ES differentiation, the present inventors raised the concentration of E-Cadherin blocking antibody was raised from 0.5 to 1 µg/mL. The results of the immunofluorescence studies indicated a similar functional trend during the first 12 days in the encapsulation microenvironment. However, as shown in FIG. 7, the net expression of neural specific markers with 1 µg/mL antibody blocking gradually increased during the differentiation process. Hepatocyte differentiation was completely diminished, while neuronal, astrocyte and oligodendrocyte marker expression was sustained and/or enhanced. Therefore disruption of cell aggregation in the alginate microcapsules induced and sustained neural specific differentiation even in the absence of the inducer retinoic acid, which provided an additional level of differentiation control for all three neural lineage populations.

Example 7

Depolymerization and Cell Recovery

Alginate microcapsules were washed with PBS and then incubated with $Ca^{2+}$ free IMDM medium (Invitrogen) containing 100 mM sodium citrate, 10 mM MOPS and 27 mM NaCl (all from Sigma-Aldrich) for 30 minutes at 37° C. to induce depolymerization. The released cells were centrifuged at 1,200 rpm for 6 minutes, the sodium citrate solution was aspirated, the cell pellet was washed with PBS buffer twice, and responded in cell specific media. The cells were counted using the method of trypan blue exclusion.

Example 8

Characterization of Mechanical Properties

The local mechanical properties of polyacrylamide substrates were quantified by measuring the elastic modulus using spherical inclusions. A small steel ball with a diameter of 1/16″ was suspended in 500 µL of gel. A calibrated magnetic force was applied to the ball and the displacement was measured with a video microscope. The calibration was performed by measuring the voltage required by the electromagnet to hold the steel ball submerged in water against the force due to gravity using a calibrated electromagnet, and the displacements of the bead were measured using a calibrated electromagnet, from which the elastic modulus E was calculated using equation $$E = \frac{\rho}{2\pi R_0}\left(\frac{F}{\delta}\right)$$

where δ is the displacement, $R_0$ is the radius of the bead and ρ is a geometrical factor, which for the infinite medium with perfect bonding is 1.0. In general, ρ is a complicated function of Poison's ratio and the parameters characterizing the boundaries. From the direct compression experimental tests, the value of ρ for the experimental setup was found to be 0.9674 (Li, L., et al., *Ann. Biomed. Eng.*, 36(5):865-876 (2008)).

To measure the compressive modulus, bulk alginate gels were prepared in 50 ml conical tubes and cut into a cylindrical disks of 30 mm diameter and 20 mm thickness with flat and parallel surfaces. Compression testing was performed at room temperature using an Instron-5542 (Instron Corporation, Canton, Mass.) instrument (Kuo, C. K. and Ma, P. X., *Biomaterials*, 22(6):511-521 (2001)). The compressive strain was set to a maximum 40% and the crosshead speed was 5 mm/min. Compressive stress (MPa), strain (%), extension (mm) and load (N) were recorded using Merlin materials testing software (Instron Corporation, Canton, Mass., USA). A total of 5 samples were tested for each concentration and the average was used to generate a force versus displacement curve. A linear fit was imposed on the curves from which a linear correlation factor was determined.

Example 9

Alcian Blue Staining

A modified alcian blue staining protocol was adapted (Powell, K. R., et al., *Anal. Biochem.*, 119(1):31-37 (1982)). Empty microcapsules were incubated with 10 mg/mL alcian blue dye at pH 5.6 in 0.3M $MgCl_2$ solution for 24 hours, and washed three times for 10 minutes in deionized water. Bright field images were acquired using an Olympus IX 81 and Olympus digital camera. 10 z-sectional images were taken for each microcapsule with a step size of 5 µm. 3-D surface view images were generated and crosslinking density was measured using Olympus Microsuite imaging analysis software. Three experiments incorporated an analysis of 10 beads per experiment.

Example 10

Intracapsular Aggregate Size Determination

Microcapsules were sampled from the tissue culture treated T-25 flasks and transferred to a 24 well plate on analysis days 4, 8, 12, 16 and 20. Bright field images were acquired using an Olympus IX70 microscope and an Olympus digital camera. For each microcapsule, 5 z-sectional images were taken at 50 µm intervals to avoid multiple quantification of the same aggregate, for a total depth of 250 µm. Image quantification was conducted using Olympus Microsuite imaging analysis software.

Example 11

Intracapsular Immunofluorescent Staining

Encapsulated cells were washed with PBS (Gibco) and fixed on days 4, 8, 12, 16 and 20 with 4% paraformaldehyde to evaluate surface proteins or together with 0.25% Triton-X to evaluate intracellular protein expression. Cells were incubated with A2B5 (1:250, Chemicon), neurofilament 160 kD (1:200, Chemicon), GFAP (1:50, Abcam, Cambridge, Mass.) and O1 (1:500, R&D Systems, Minneapolis, Minn.)

overnight at 4° C. in PBS buffer containing 1% normal goat serum for surface proteins or with together with 0.25% Triton-X for intracellular proteins. The microcapsules were washed three times for 10 minutes in PBS buffer, and then treated with secondary antibody, FITC-conjugated goat anti-rabbit IgG or anti-mouse IgM (both 1:500, Invitrogen) for 2 hours at room temperature. Normal immunoglobulin served as control for non-specific antibody binding, whose fluorescence intensity was subtracted from overall intensity of the antibody expression.

To detect cell surface adhesion molecule E-Cadherin, encapsulated cells were incubated with FITC-conjugated mouse anti-mouse E-Cadherin antibody (1:500, BD Biosciences), or mouse $IgG_{2a}$ (1:500, BD Biosciences) as an isotype control. They were then both washed with PBS three times for 10 minutes. For both stains, fluorescent images were acquired with an Olympus IX70 microscope and an Olympus digital camera using an excitation filter of 515 nm. Image quantification was conducted using Olympus Microsuite imaging analysis software.

Example 12

Antibody Blocking Experiments

To prevent the formation of aggregates, E-Cadherin (BD Biosciences) antibody was added at a concentration of 0.5 μg/mL or 1 μg/mL to a 5 mL culture sample of microcapsules for 4, 8, 12, 16 and 20 days. As a control for non-specific blocking of cell adhesion molecules a mouse $IgG_{2a}$ at 0.5 μg/mL or 1 μg/mL (BD Biosciences) was utilized in a separate 5 mL sample of microcapsules.

Example 13

PPAR Agonists Accelerate Oligodendrocyte Differentiation of Mouse Embryonic Stem Cells Undifferentiated Cell Culture The ES cell line D3 (ATCC, Manassas, Va.) was maintained in an undifferentiated state in T-75 gelatin-coated flasks (Biocoat, BD-Biosciences, Bedford, Mass.) in Knockout Dulbecco's Modified Eagles Medium (Gibco, Grand Island, N.Y.) containing 15% knockout serum (Gibco), 4 mM L-glutamine (Gibco), 100 U/mL penicillin (Gibco), 100 U/mL streptomycin (Gibco), 10 μg/mL gentamicin (Gibco), 250 U/mL ESGRO™ (Chemicon, Temecula, Calif.), 0.1 mM 2-mercaptoethanol (Sigma-Aldrich, St. Louis, Mo.). ESGRO™ contains leukemia inhibitory factor (LIF), which prevents embryonic stem cell differentiation. Every 2 days, media was aspirated and replaced with fresh media. Cultures were split and passaged every 5-6 days, following media aspiration and washing with 6 mL of phosphate buffered solution (PBS) (Gibco). Cells were detached following incubation with 2 mL of trypsin (0.25%)—EDTA (Gibco) for three min, resulting in a single-cell suspension, followed by the addition of 8 mL of Knockout DMEM. The 10 mL cell solution was then centrifuged at 1000 rpm for 5 minutes, the supernatant aspirated and the pellet re-suspended in 1 mL. The cells were re-plated in gelatin-coated T-75 flasks at a density of $1\times10^5$ cells/mL.

Differentiation Cell Culture

Two Dimensional Differentiation:

In order to induce differentiation, cells were replated into gelatin coated 6 well plates (Biocoat, BD-Biosciences, Bedford, Mass.) at a density of $1\times10^4$ cells/cm². Cells were placed in DMEM/F12 (Invitrogen, Carlsbad, Calif.) media supplemented with 1% N-2 (Invitrogen—contains human transferrin, insulin, progesterone, putrescine and selenite), 100 U/mL penicillin and 100 U/mL streptomycin for 8 days. Every 2 days, media was aspirated and replaced with fresh media. On day 8, the cells were replated at a density of $0.5\times10^4$ cells/cm² into 24 well plates (Falcon, BD Biosciences, San Jose, Calif.) that were precoated with 0.1% Gelatin (Sigma-Aldrich) for 1 hour at 37° C. To aid in cell attachment, 10 ng/ml basic fibroblast growth factor (bFGF) was added. From day 8 to day 16, 1% Fetal Bovine Serum (FBS-Invitrogen) is added. Every 2 days, media was aspirated and replaced with fresh media.

Figure 9:
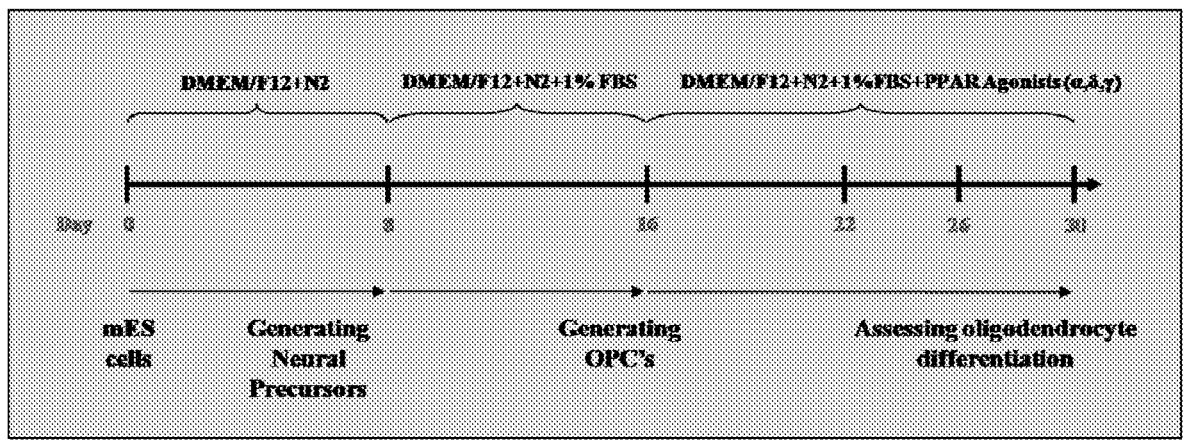
FIG. 9 illustrates a two dimensional (2D) monolayer differentiation protocol.

PPAR Agonist Addition (2D):

On day 16, the cells are replated at a density of $0.5\times10^4$ cells/cm² into the same differentiation media supplemented with either 10 μM PPAR alpha (Sigma-Aldrich: WY-14643), 1 μM PPAR delta (Sigma-Aldrich: GW0742), or 10 μM PPAR gamma (Sigma-Aldrich: GW1929). All three agonists were dissolved in 0.05% DMSO (Sigma-Aldrich). Every 2 days, media was aspirated and replaced with fresh media with agonists. Cells were fixed for immunofluorescence analysis on Days 22, 26 and 30. See FIG. 9.

All cell cultures were incubated in a humidified 37° C., 5% $CO_2$ environment.

Three Dimensional Differentiation—Alginate Poly-L-Lysine Encapsulation:

The alginate encapsulation process was done using the protocol setup by Maguire, T., et al., *Biotechnol. Bioeng.*, 93(3):581-91(2006). Briefly, an alginate solution was generated by dissolving 2.2 g of alginate (Sigma-Aldrich, MW: 100,000-200,000 g/mol, GContent: 65%-70%) in 100 mL of $Ca^{2+}$ free DMEM, using a heated magnetic stir plate at a temperature of 45° C. The solution was then filtered using a 25-micron syringe filter (Fisher Brand, Pittsburgh, Pa.). A confluent monolayer of undifferentiated ES cells were removed following trypsin incubation, centrifuged for 10 min at 1,000 rpm, and resuspended in PBS. The cells were washed twice more with PBS, resuspended in 2 mL of their respective media (IMDM, IMDM+Retinoic Acid (RA) ($1\times10^{-7}$M), DMEM/F12+N2) and both cell number and viability assessed using the method of trypan blue (Gibco) exclusion. To create the cell-alginate mixture, 1 mL of cell suspension with a density of $50\times10^6$ cells/mL was added to 9 mL of a 2.2% (w/v) alginate solution to yield a final cell density of $5\times10^6$ cells/mL and a final alginate concentration of 2.0% (w/v). This solution was transferred to a 10 mL syringe (BD Biosciences), which, in turn was connected to a syringe pump (KD Scientific, Holliston, Mass.). Alginate beads were generated using an electrostatic bead generator (Nisco, Zurich, Switzerland) at a flow rate of 40 mL/h, and an applied voltage of 6.5 kV, resulting in beads with a diameter of 500 μm. The beads were collected in a 200 mL bath of $CaCl_2$ (100 mM) (Sigma-Aldrich), containing 145 mM NaCl (Sigma-Aldrich), and 10 mM MOPS (Sigma-Aldrich) and were left to polymerize for 10 minutes at room temperature. Beads were transferred to a tissue culture treated 1-25 flask (Falcon, BD Biosciences), following the polymerization step. The $CaCl_2$ solution was removed using a 5 mL pipette, and the beads were washed with 5 mL of HEPES (Gibco). The HEPES was removed and the beads were re-suspended in 5 mL of poly-L-lysine (PLL) (Sigma-Aldrich, MW: 68,600 g/mol) (0.05% w/v) for 2 min. The PLL was then gently removed, replaced with HEPES to wash the beads and the beads were ultimately re-suspended in 5 mL of cell culture media. Media was changed every 4 days post-encapsulation. In all experimental conditions, monolayer culture configurations were used as controls.

Figure 10:
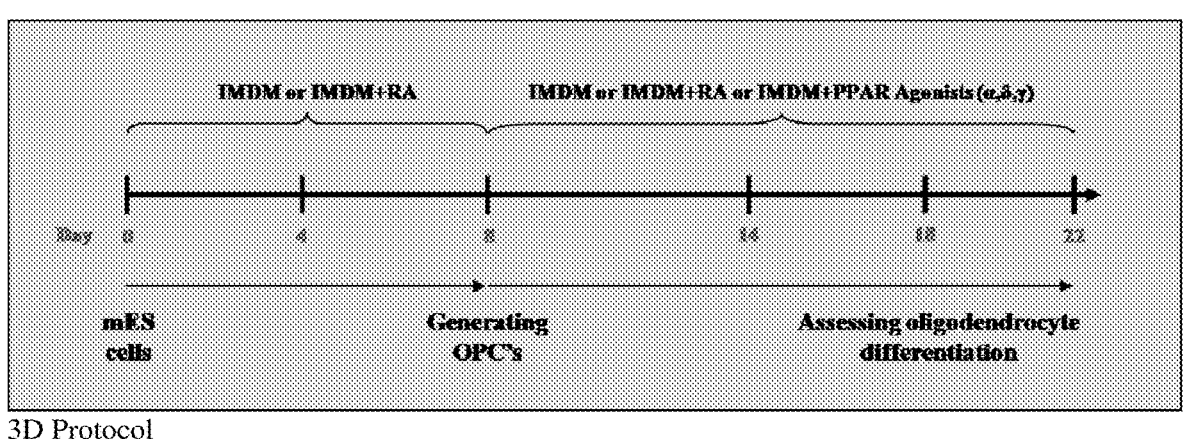
FIG. 10 illustrates a three dimensional (3D) differentiation protocol using alginate poly-L-lysine encapsulation.

PPAR Agonist Addition (3D):

On day 8, the differentiation media was supplemented with either 10 μM PPAR alpha (Sigma-Aldrich: WY-14643), 1 μM PPAR delta (Sigma-Aldrich: GW0742), or 10 μM PPAR gamma (Sigma-Aldrich: GW1929). All three agonists were dissolved in 0.05% DMSO (Sigma-Aldrich). Cells were fixed for immunofluorescence analysis on Days 8, 14, 18 and 22. See FIG. 10.

In Situ Indirect Immunofluorescent Analysis

Cells were fixed before doing any immunofluorescence. This was done by first washing the cells 3 times in Tris Buffered Saline (TBS) followed by incubating the cells in 4% paraformaldehyde (Sigma-Aldrich) for 15 minutes at room temperature. The cells were again washed 3 times in TBS for 5 minutes at room temperature). In order to reduce non-specific binding of the antibodies to proteins on/within the cells, they were first blocked for 45 minutes at room temperature by incubating the cells with TBS, 10% goat serum (Invitrogen), 1% Bovine Serum Albumin (BSA-Sigma) and depending on if the protein in question is intracellular, 0.1% Triton X-100. The cells were then incubated overnight at 4° C. with the respective primary antibody in TBS, 1% goat serum and if the protein in question was intracellular, 0.1% Triton X-100. The antibodies used were: 5 μg/ml mouse anti-A2B5 IgM (Chemicon), 2 μg/ml mouse anti-O1 IgM (R&D Systems, Minneapolis, Minn.), 12.6 μg/ml mouse anti-CNPase (2', 3'-cyclic nucleotide 3'-phosphodiesterase) IgG1 (Sigma) and 8 μg/ml rabbit anti-Myelin Basic Protein IgG (MBP—abcam, Cambridge, Mass.). To account for non-specific binding, isotype controls were used for each antibody: for A2B5 and O1—mouse IgM (Chemicon), for CNPase—mouse IgG1 (BD Biosciences) and for MBP—rabbit IgG (Invitrogen). The cells were washed 3 times for 5 minutes in TBS and if the protein in question was intracellular, 0.1% Triton X-100×-100. The cells were then incubated for 1 hour at room temperature with the respective secondary in TBS and if the protein in question is intracellular, 0.1% Triton X-100. The secondaries used were: for A2B5 and O1—Alexa Fluor 488 goat anti-mouse IgM (Invitrogen—1:500), CNPase—Alexa Fluor 488 goat anti-mouse IgG1 (Invitrogen—1:500) and MBP—Alexa Fluor 488 goat anti-rabbit IgG (Invitrogen—1:500). The cells were then washed 2 times in TBS for 5 minutes at room temperature. The cells were counterstained with Hoechst 33342 (Invitrogen) for 10 minutes at room temperature (1 μg/ml).

Oil Red O Staining

After the cells were fixed using 4% paraformaldehyde, they were then washed twice with PBS and rinsed once with 60% isopropanol (Sigma) for 5 minutes. A 0.18% Oil Red O (Sigma) solution in $diH_2O$ was then added to the cells for 10 minutes (diluted down from a 0.3% stock solution of Oil Red O in 99% isopropanol and filtered through filter paper). The cells were then rinsed several times with PBS (30 second rinses) until all excess Oil Red O was removed. Cells were counterstained with Hoechst 33342 (Invitrogen) for 10 minutes at room temperature (1 μg/ml). Images were taken using an Olympus CKX-41 microscope with an Olympus Magnafire Color Camera and Magnafire software v.2.1C.

Fluorescent Images and Image Analysis

Fluorescent images were acquired using a computer interfaced inverted Olympus IX70 microscope. Specimens were excited using a 488 nm filter. Fluorescent intensity values were determined for each cell using Olympus Microsuite™ software. Experimental intensity values for each cell were calculated after subtracting the average intensity of the isotype control.

Statistical Analysis of Functional Assays

Each data point represents the mean of three or greater experiments, and the error bars represent the standard deviation of the mean. Statistical significance was determined using the Student's t-test for unpaired data. Differences were considered significant if the P-value was less than or equal to 0.05.

ES Cell Differentiation into Immature Oligodendrocytes

Figure 11:
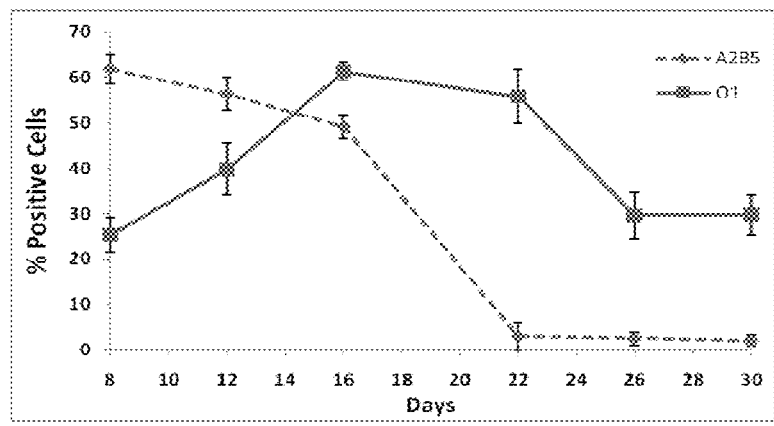
FIG. 11 illustrates the percentage of cells that are positive for A2B5 or O1. A monolayer of ESD3 cells exposed to DMEM/F12 and N2 for 8 days and then supplemented with 1% FBS for the remainder of the experiment. Values represent averages of at least four separate experiments and error bars represent standard error of the means.
Figure 12A:
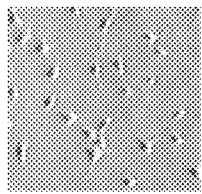
FIGS. 12A, 12B, 12C and 12D illustrate 2D cell morphology on day 30 (14 days of PPAR agonist).
Figure 12B:
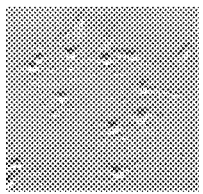
Figure 12C:
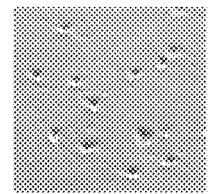
Figure 12D:
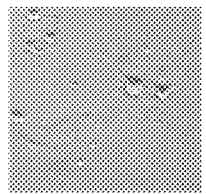

Using a two dimensional monolayer differentiation protocol adapted from Ying et al. (Ying, Q. L., et al., *Nat. Biotechnol.*, 21(2):183-6 (2003)), pluripotent mouse ESD3 cells were differentiated into oligodendrocyte progenitor (A2B5 positive) and immature oligodendrocyte (O1 positive) cells. This was done using DMEM/F12 media supplemented with N-2 (i.e. Bottenstein's formulation) for 8 days, thereafter replating the cells and adding 1% FBS. FIG. 11 shows that after the exposure to N-2 for an initial 8 days, the cells are approximately 62% and 25% positive for the oligodendrocyte progenitor marker A2B5 and the immature oligodendrocyte marker O1 respectively. The expression of A2B5 steadily decreases from Day 8 through to Day 16 (49%) where it dramatically drops off to almost zero (3%) by Day 22. O1 expression however steadily increases from Day 8 to a peak of 61% at Day 16 where it stays relatively level until Day 22 (56%), thereafter it drops and levels off at 30% after Day 26. This expression profile seems to indicate an initial progression or maturation from progenitor to an immature oligodendrocyte state. Although the mature oligodendrocyte marker Myelin Basic Protein (MBP) was not expressed by cells. The data are also listed in Table 2 below.

TABLE 2

| The percentage of cells that are positive for A2B5 or O1. | | | | | | |
|---|---|---|---|---|---|---|
| | Day 8 | Day 12 | Day 16 | Day 22 | Day 26 | Day 30 |
| A2B5 | 61.8 ± 3.2 | 56.4 ± 3.7 | 49.2 ± 2.6 | 3.0 ± 3.0 | 2.5 ± 1.4 | 2.0 ± 1.2 |
| O1 | 25.4 ± 3.8 | 39.8 ± 5.7 | 61.3 ± 1.9 | 55.9 ± 5.8 | 29.6 ± 5.2 | 29.8 ± 4.4 |

Addition of PPAR Agonists

In order to assess if PPAR's have an effect on oligodendrocyte differentiation, agonists for the three known receptors were added to cell cultures. PPAR agonists (α, δ, γ) were supplemented into differentiation media to assess either initiation (Day 8) or acceleration (Day 16) effects on differentiation. The agonists appeared to have no effect on differentiation when added on Day 8 (refreshed every 2 days till Day 30) (data not shown). However, when added on Day 16 (peak O1 expression), and refreshed every 2 days till Day 30, we see a distinct change in both morphology (FIG. 12) and in the accelerated expression of more mature oligodendrocyte markers (FIG. 13). FIG. 12 shows variations in cell morphology with respect to the three different PPAR agonists on Day 30, i.e. after 14 days of agonist exposure. In the case of the control cells we see that a few cells are either extending processes, are bipolar or have no distinct morphology. When PPAR alpha is added, we see that the majority of cells have extended processes with some having secondary branching, we also see an increase in the number of processes per cell compared to control. When PPAR delta is added, we see that the majority of cells have extended processes with some having secondary branching, but when comparing to PPAR alpha cells, these processes seem to be longer in length. When PPAR gamma is added, we see two distinct morphologies occurring. The majority of the cells are large and spread out with another smaller population of cells that have a developed secondary and tertiary branched structure. There was a significant increase in cell death in the PPAR gamma case as compared to all other cases, as evident in the cell density in the representative image.

Figure 13A:
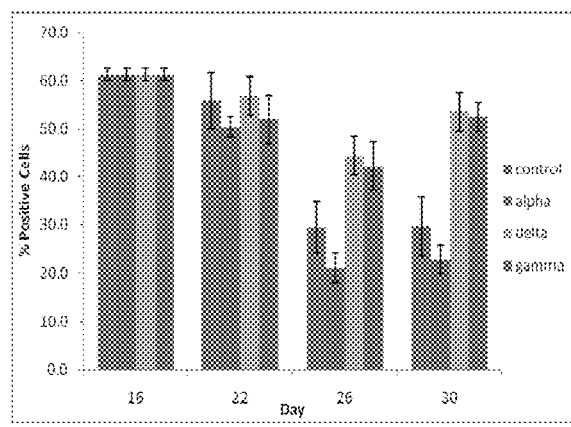
FIGS. 13A and 13B illustrate expression of O1 and CNPase after exposure to PPAR agonists. A monolayer of ESD3 cells were exposed to DMEM/F12 supplemented with N2, 1% FBS and PPAR agonists. A) Percentage of cells positive for O1 over time, B) Percentage of cells positive for CNPase over time. Control represents cells that were not exposed to the agonist. These results represent averages of at least four separate experiments and error bars are standard error of the means.
Figure 13B:
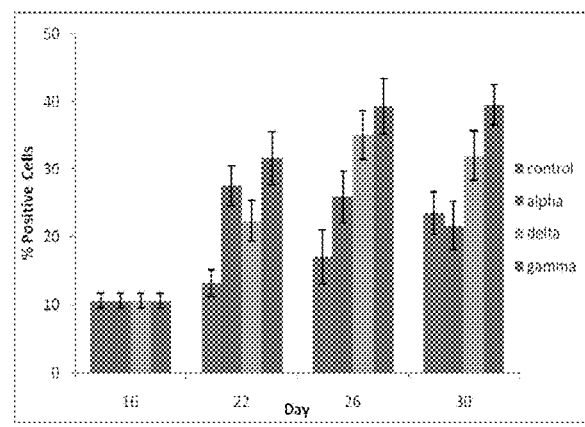

The expression of oligodendrocyte specific markers is shown in FIG. 13. The expression of O1 and CNPase was assessed over a 14 day time period after the exposure to PPAR agonist's alpha, delta and gamma (i.e., from Day 16-Day 30). FIG. 13A shows how O1 and CNPase vary over time for PPAR alpha with respect to control. As can be seen, the control cells show a gradual tapering of O1 expression with a corresponding increase in CNPase expression. After the addition of PPAR alpha, O1 expression drops consistently over the 14 day period, while CNPase expression increases over the initial 6 days and stabilizes for the remaining 8 days. FIG. 13B shows how O1 and CNPase vary over time for PPAR delta with respect to control. After the addition of PPAR delta, O1 expression drops sharply over the last 8 days, whereas CNPase expression gradually increases over the 14 day period. FIG. 13C shows how O1 and CNPase vary over time for PPAR gamma with respect to control. After the addition of PPAR gamma, O1 expression gradually tapers over the 14 day period, whereas CNPase expression has a large increase over the initial 10 days thereafter stabilizing. Of the three agonists, PPAR gamma experiences the largest increase in CNPase by Day 26 (with respect to control). The effect of the agonist solvent DMSO (0.05%) on differentiation is negligible, i.e. not statistically significant to the untreated control cells (data not shown).

Figure 14:
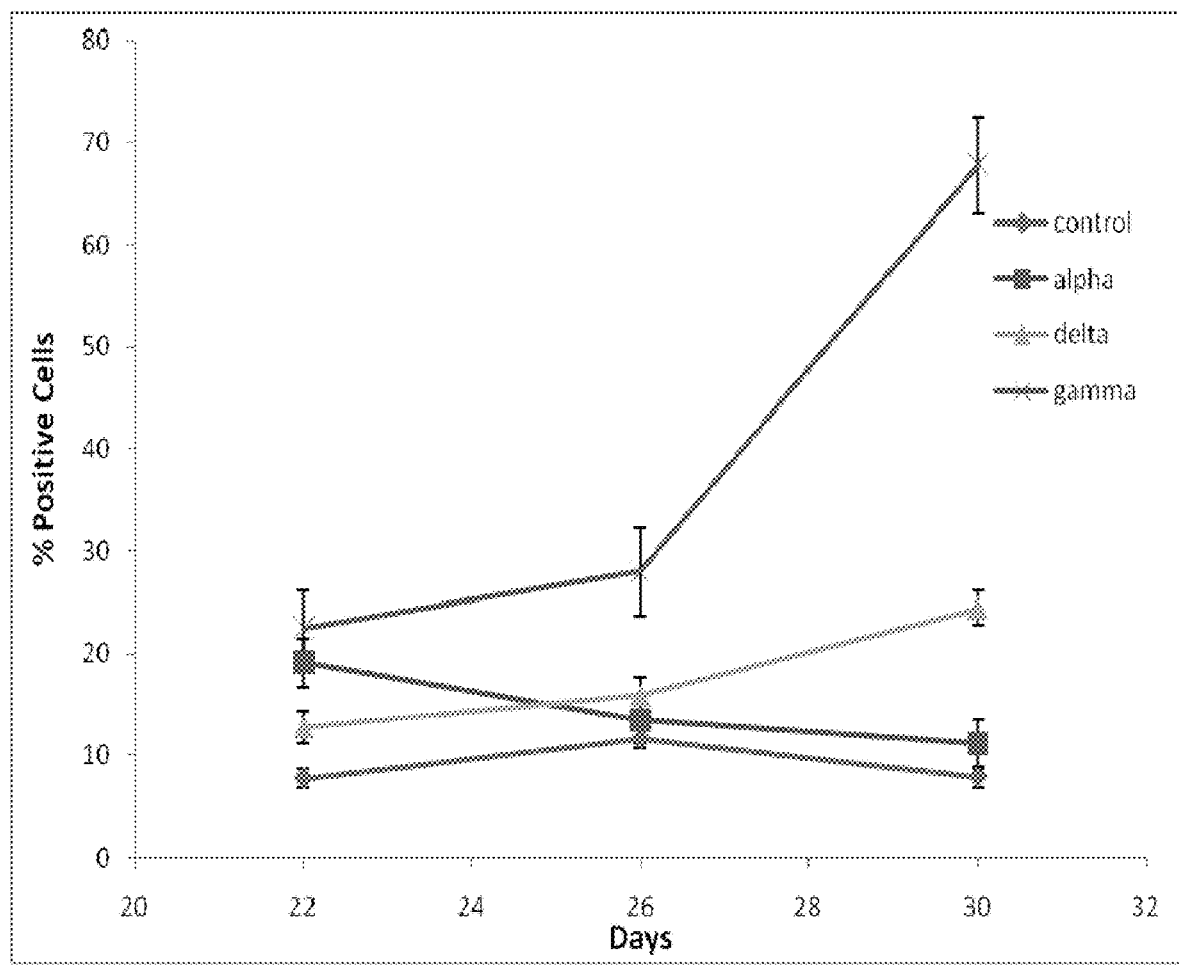
FIG. 14 illustrates Oil Red O Stain. A monolayer of ESD3 cells were exposed to DMEM/F12 supplemented with N2, 1% FBS and PPAR agonists. Control represents cells that were not exposed to the agonist. Error bars represent standard error of the mean.

Oil Red O is a fat-soluble dye used for the staining of neutral triglycerides and lipids and among other things is used to detect myelin and myelin degradation products (Boven, L. A., et al., Brain, 129(Pt 2):517-526 (2006); Zou, T., et al., J. Neuropathol. Exp. Neurol., 65(1):78-86 (2006)). FIG. 14 shows the detection of these lipids over the last 8 days of agonist supplementation. PPAR alpha seems to have minimal effect compared to control, whereas by Day 30, both PPAR delta and gamma are significantly higher than control.

3-Dimensional Culture Environment

3D+N2:

FIG. 13B shows that it takes 22 days before we start to see an increase in the expression of the oligodendrocyte marker CNPase with only a maximum of approximately 40% being seen by day 30. Throughout this time period no expression of the mature oligodendrocyte marker Myelin Basic Protein (MBP) is seen. It was hypothesized that one reason for not maturing to the stage of being able to express MBP could be due to a sub-optimal non-physiological two dimensional (2D) environment. Thus cells were placed inside a three dimensional (3D) alginate bead (previously been shown to be capable of producing either hepatocytes or neuronal lineage cells) (Maguire, T., et al., Biotechnol. Bioeng., 93(3):581-91(2006)). Results of experiments where cells were exposed to DMEM/F12 supplemented with N2 for 8 days and thereafter further supplemented with 1% FBS (2D protocol) till day 16 can be seen in Table 3. When comparing A2B5 and O1 expression to those obtained in the 2D case (FIG. 13), we see that in the 3-D environment less cells express the respective marker, i.e. A2B5 peaks at ~26% vs. ~60% and O1 peaks at ~28% vs ~60%. When we look at the more mature marker CNPase, we see that the expression in the 3D environment peaks at ~40% within 16 days as compared to 30 days in the 2D case. What is promising is that MBP expression is seen for the first time, peaking at ~30%, indicating that the cells are maturing further within the 3D capsules.

TABLE 3

A2B5, O1, CNPase and MBP Expression of DMEM/F12 + N2 Encapsulated Cells. Cells were exposed to DMEM/F12 + N2 + 1% FBS for 16 days and the expression of A2B5, O1 CNPase and MBP assessed. The values are averaged from 2 separate experiments (except MBP-1 experiment) ± standard error of the mean.

| | DMEM/F12 + N2 + 1% FBS | | | |
|---|---|---|---|---|
| | A2B5 | O1 | CNPase | MBP |
| Day 8 | 25.5 ± 3.2 | 28.2 ± 4.1 | 27.8 ± 4.2 | 29.60 |
| Day 16 | 18.9 ± 4.2 | 10.2 ± 2.9 | 39.9 ± 5.6 | 20.00 |

3D+RA:

The differentiation of ES cells into MBP expressing cells using DMEM/F12 and N2 was compared to the well known differentiation system using IMDM and RA. Table 4 shows the results of A2B5, O1, CNPase and MBP expression in cells exposed to RA for 16 days. From this table we see that exposure to RA results in higher expression of A2B5 (44%) and O1 (32%) as compared to DMEM/F12+N2, although a slightly lower expression of CNPase (32%) is seen. The expression of MBP is however higher and is sustained for a longer time period.

TABLE 4

A2B5, O1 CNPase and MBP Expression of IMDM and RA Encapsulated Cells. Cells were exposed to of to IMDM supplemented with Retinoic Acid for 16 Days and the expression of A2B5, O1, CNPase and MBP was assessed. The values are averaged from 3 separate experiments ± standard error of the mean.

| | IMDM + RA | | | |
|---|---|---|---|---|
| | A2B5 | O1 | CNPase | MBP |
| Day 8 | 30.4 ± 4.3 | 22.5 ± 3.2 | 18.1 ± 3.6 | 35.3 ± 4.3 |
| Day 12 | 26.3 ± 1.9 | 32.4 ± 5.4 | 32.1 ± 4.2 | 25.3 ± 1.8 |
| Day 16 | 13.3 ± 3.7 | 20.9 ± 5.6 | 23.4 ± 5.9 | 29.0 ± 2.3 |

Figure 15A:
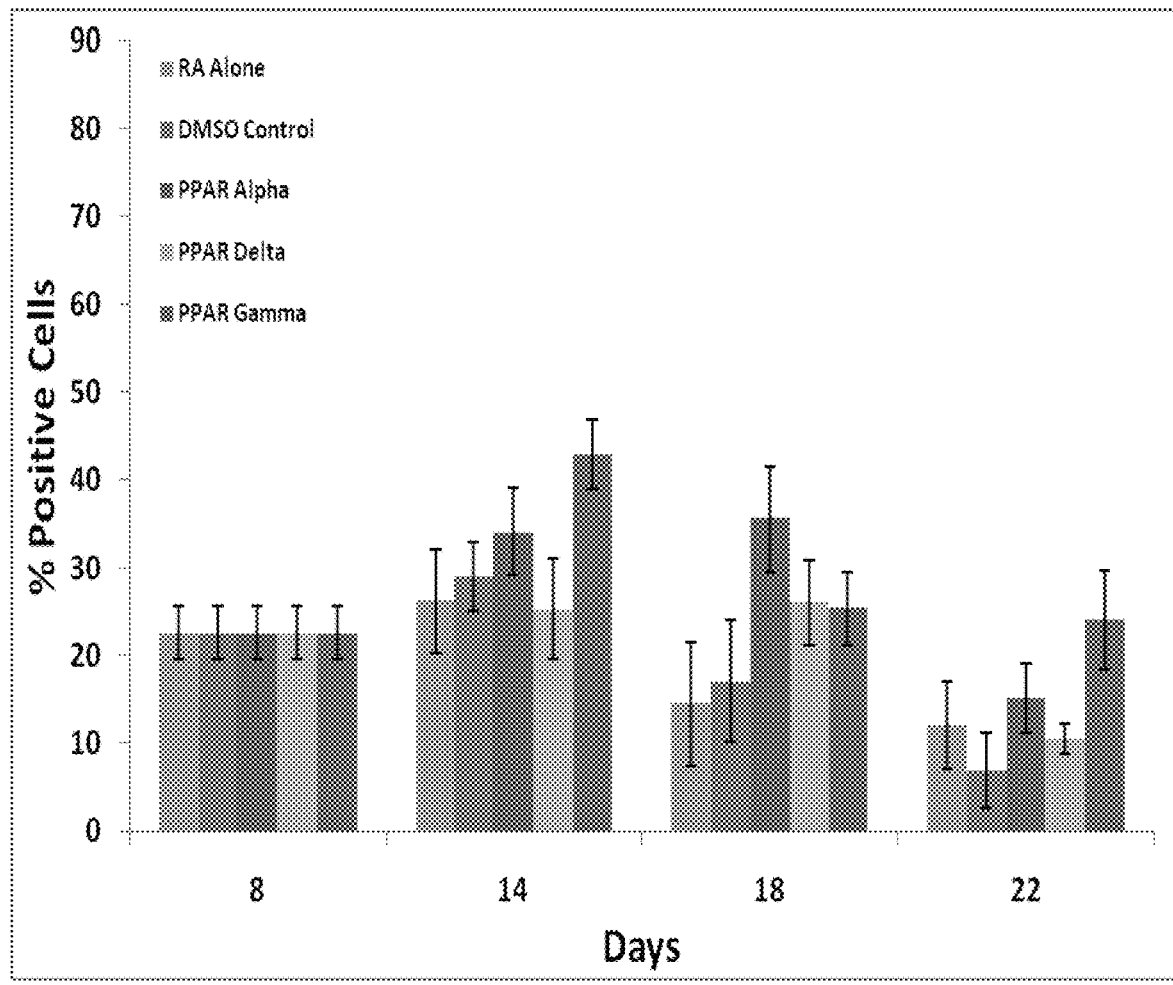
FIGS. 15A, 15B and 15C illustrate O1, CNPase and MBP expression of IMDM and RA encapsulated cells. Cells were exposed to IMDM with Retinoic Acid for 8 Days and then supplemented with either DMSO (0.05%) or PPAR agonists (alpha, delta, gamma). The expression of O1 (FIG. 15A), CNPase (FIG. 15B) and MBP (FIG. 15CC) was assessed. The values are averaged from 2 separate experiments±standard error of the mean.
Figure 15B:
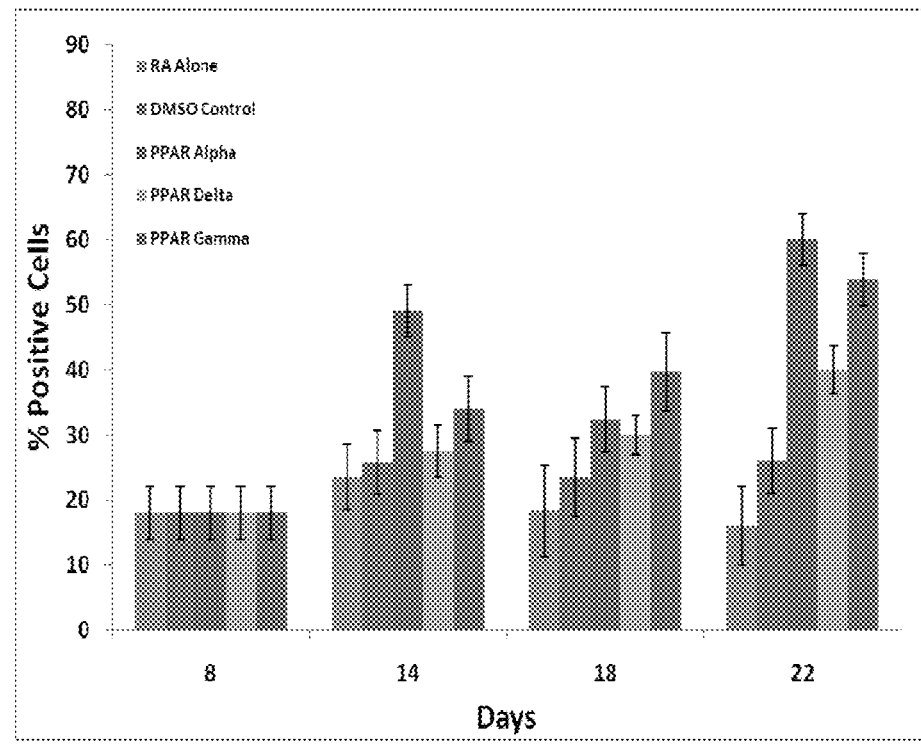
Figure 15C:
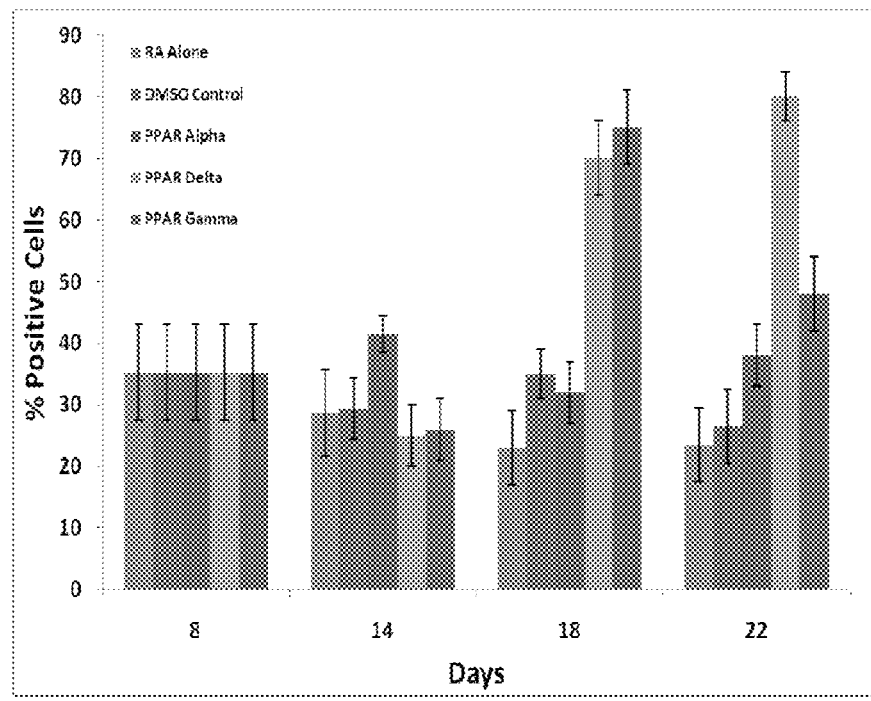

3D+RA+PPAR Agonists:

In order to see if MBP expression could be enhanced or sustained, PPAR agonists (alpha, delta, gamma) were added to cells exposed to IMDM and RA for 8 days. The agonists were added to the cells for 14 days and the expression of O1, CNPase and MBP was assessed over time (6 days, 10 days and 14 days). FIGS. 15A, 15B, and 15C show how these markers vary. From the FIGS. 15A, 15B, and 15C) we see that with RA alone O1 expression seems to steadily decrease over time, while CNPase stays pretty constant (i.e. not statistically significantly different), MBP expression initially decreases and then stays pretty constant. The DMSO control (agonist solvent—0.05%) does not seem to have a significant effect on differentiation apart from CNPase expression on Day 22 and MBP expression on Day 18 (0.065% DMSO has been seen to have some effect on thyroid hormone induced oligodendrocyte differentiation on neurospheres when cells were stained for 04 (Fritsche, E., et al., *Environ. Health Perspect.*, 113(7):871-6 (2005)). PPAR alpha exposed cells show a peaking (~35%) on day 18 of O1 expression and then a drop off to ~15% on day 22. CNPase expression is biphasic with a peak in expression on day 22 with about 60% demonstrating some level of maturation. However MBP expression stays pretty constant over the time period. PPAR delta exposed cells stay pretty constant from Day 8 to 18 and then a drop off at Day22 with O1 expression. CNPase expression steadily increases over time peaking on day 22 with about 40%. MBP expression shows a rapid increase on day 18 and sustaining high levels of expression with a peak on day 22 with ~80%. PPAR gamma exposed cells show an initial peak in O1 expression on day 14 (about 42%) with a drop off to about 22% on day 22. CNPase expression increases steadily over time similar to delta case but at a greater rate (~53%). MBP expression peaks on day 18 at about 74% but then drops off to about 45% on day 22.

PPAR delta exposed cells seem to be the best condition that exhibits a good differentiation progression to a high MBP expressing state that is capable of being sustained. This condition was thus selected to see if it could be further optimized by looking at various concentrations of the delta agonist (0.1 µM, 1 µM and 10 µM). No significant differences could be seen at the three various concentrations (data not shown).

Example 14

MSC Cell Culture hMSCs were purchased from Texas A&M University. Cells were grown in Alpha-MEM supplemented with 10% MSCs qualified FCS, 2 ng/ml L-glut and 1 ng/ml bFGF. MSCs were seeded at 5000 cells/cm2 in falcon flasks and media was changed every four days.

Example 15

Alginate Micro-Encapsulation

To create the cell-alginate mixture, cells are added to an alginate solution (Sigma Aldrich, MW 100,000-200,000 g/mol, G Content: 65%-70%) to yield a final desired cell seeding density and final alginate concentration (see Maguire, T., et al., *Biotechnol. Bioeng.*, 98, 631-644, (2007)). This solution is then transferred to a 10 mL syringe and connected to a syringe pump (KD Scientific, MA). Alginate beads are generated using an electrostatic bead generator (Nisco, Zurich, Switzerland) at a flow rate of 40 mL/h, and an applied voltage of 6.5 kV. The beads are extruded into a 200 mL bath of CaCl2 (100 mM), containing 145 mM NaCl, and 10 mM MOPS (all from Sigma-Aldrich) and left to polymerize for 10 min at room temperature. The CaCl2 solution is removed using a 5 mL pipette, and the beads washed with 5 mL of HEPES (Gibco). The HEPES is removed and the beads re-suspended in 5 mL poly-L-lysine (PLL) (Sigma-Aldrich, MW 68,600 g/mol) (0.05% w/v) for 2 min. The PLL is then gently removed, replaced with HEPES to wash the beads and the beads ultimately resuspended into 5 mL of cell culture media. The microencapsulated cells are re-suspended in DMEM (Invitrogen) and transferred to 25 mm$^2$ tissue culture flasks. Media is changed every 3$^{rd}$ day post-encapsulation. In all experimental conditions, monolayer culture configurations of MSCs are used as controls for viability, growth kinetics, and functional studies. Various size ranges of microcapsules were generated (between 100-300 µm) in combination with different concentrations of alginate (1.5%, 2% and 2.5%) as well as different cell densities (1×10$^5$, 2.5×10$^5$, 5×10$^5$, 1×10$^6$, cells per mL).

Example 16

MSC Alginate Microencapsulation

Figure 24:
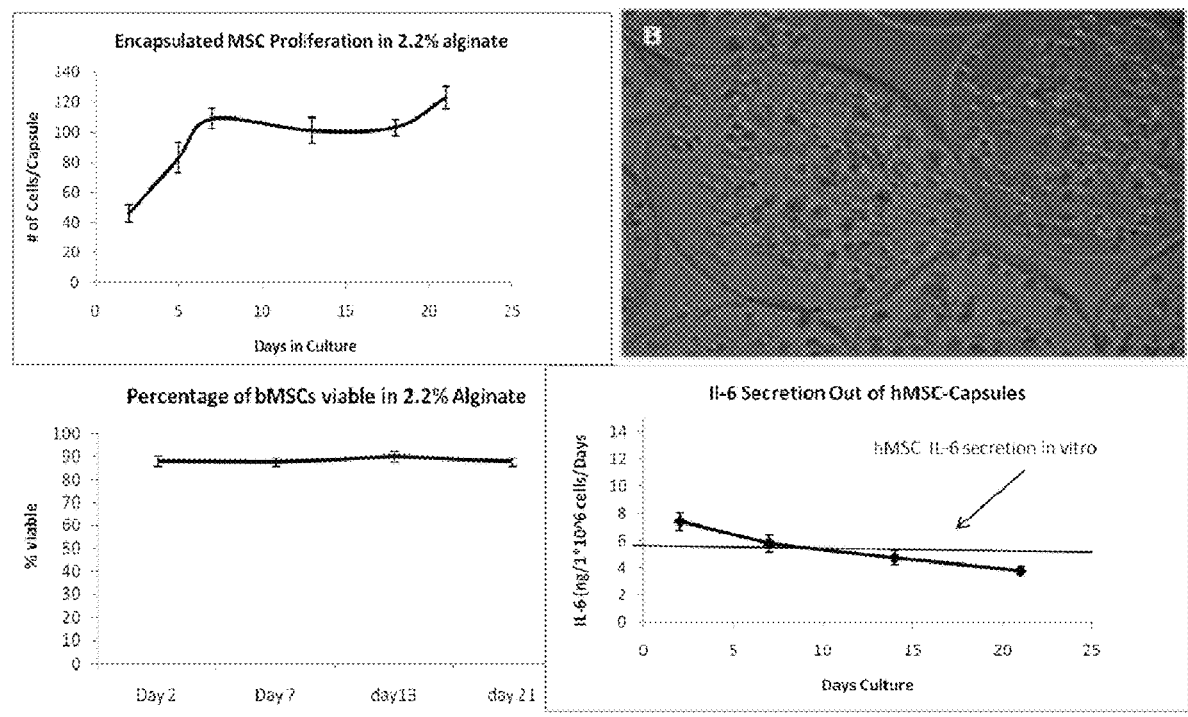
FIG. 24 illustrates MSCs in alginate capsules: A) Encapsulated MSC growth kinetics in 2.2% percent alginate over a 25 day period. B) Encapsulated MSCs remained in a non-aggregated state throughout the culture period. C) Encapsulated MSC viability remained above 90% throughout the 21-day culture period. D) IL-6 secretion out of the capsules were evaluated using ELISA. Encapsulated MSCs secrete IL-6 levels relative to control cells plated on tissue culture plastic.

The present inventors generated controlled microencapsulated stem cell cultures (Maguire, T., et al., *Biotechnol. Bioeng.*, 98, 631-644 (2007), Maguire, T., et al., *Biotechnol. Bioeng.*, 93, 581-591 (2006)) and explored using this technology for sustaining function of MSCs. Encapsulated MSCs were viable, non-aggregated, tripled in cell number and mircoencapsulation system as a vehicle to deliver MSCs (FIG. 24).

Example 17

Evaluation of Encapsulated MSC Viability

Figure 16A:
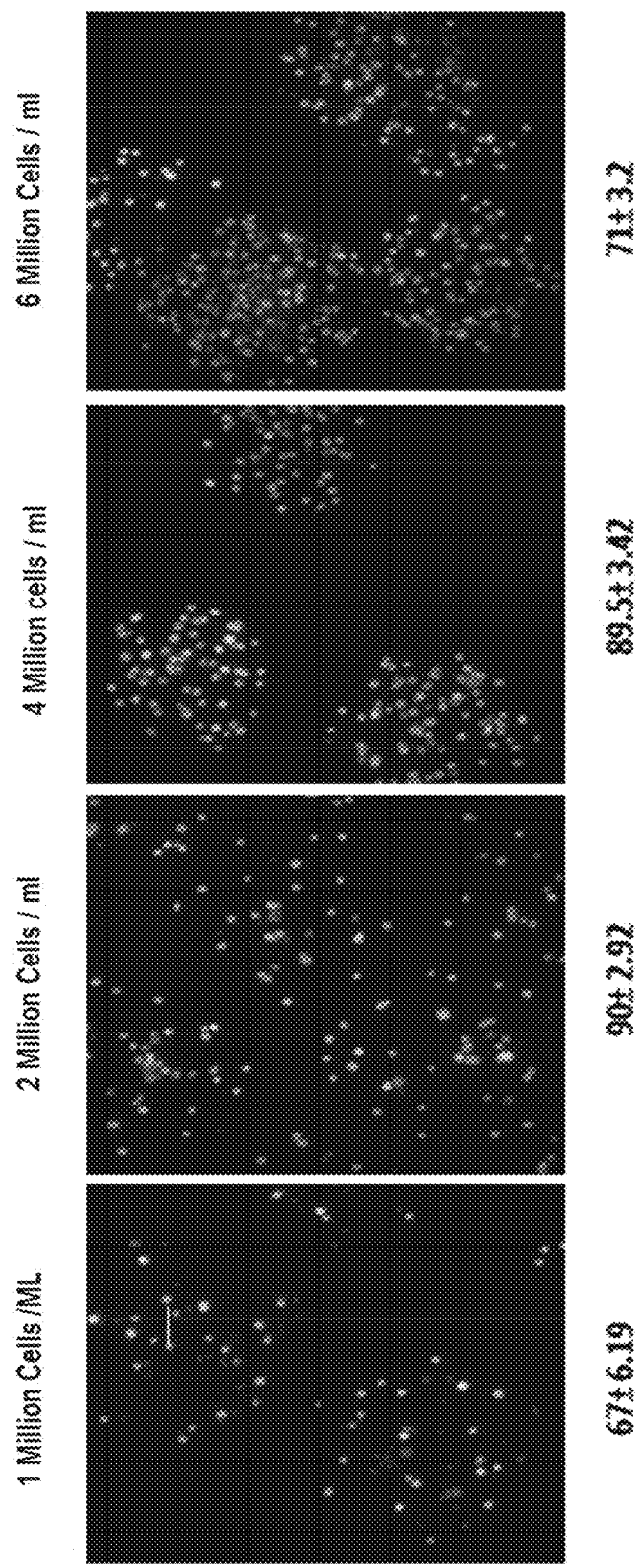
FIGS. 16A, 16B and 16C illustrate MSC viability and behavior in Alginate microcapsules.

An MSC immobilization system was developed to provide long-term functional benefit after tissue trauma. In order to fulfill this requirement several MSC properties must be supported, including sustained MSC viability over time. Therefore, initial experiments were designed to evaluate the effect of intra-capsular cell seeding density on cell viability. A combination of calcein and ethiduim homodimer staining indicated that maximum cell viability was achieved with cell seeding densities of 2-4 million cells (FIG. 16A). At cell concentrations of 1 and 6 million cells/mL a significant decrease in cell viability (FIG. 16A) was apparent. Subsequently, long term cell viability was measured and experimental results indicated that encapsulated MSCs remained greater than 90% viable for 90 days post encapsulation (FIG. 16B), indicating that the microenvironment is able to sustain MSC survival.

Viability was assessed using calcein (Molecular Probes, Eugene, Oreg.), and ethidium homodimer (Molecular Probes) staining post encapsulation. Calcein is cleaved to form fluorescent products in live cells while ethidium is only incorporated into nuclei of dead cells. Capsule images where acquired using an Olympus spinning disc microscope. 500 um Z stacks were acquired at 20 um intervals for 10 capsules per condition. Each section was quantified using slidebook analysis software.

Example 18

Evaluation of Encapsulated MSC Proliferation

Figure 16C:
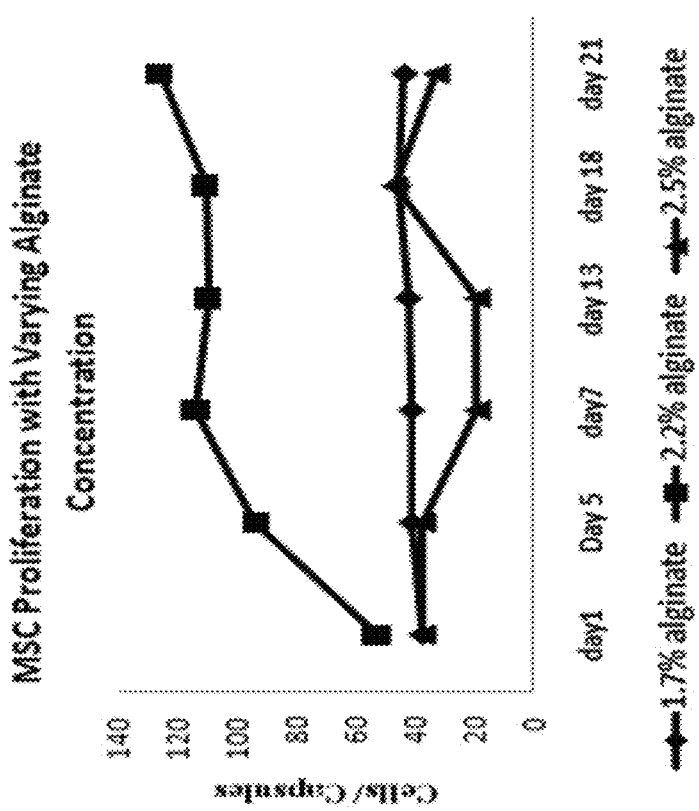
Figure 16B:
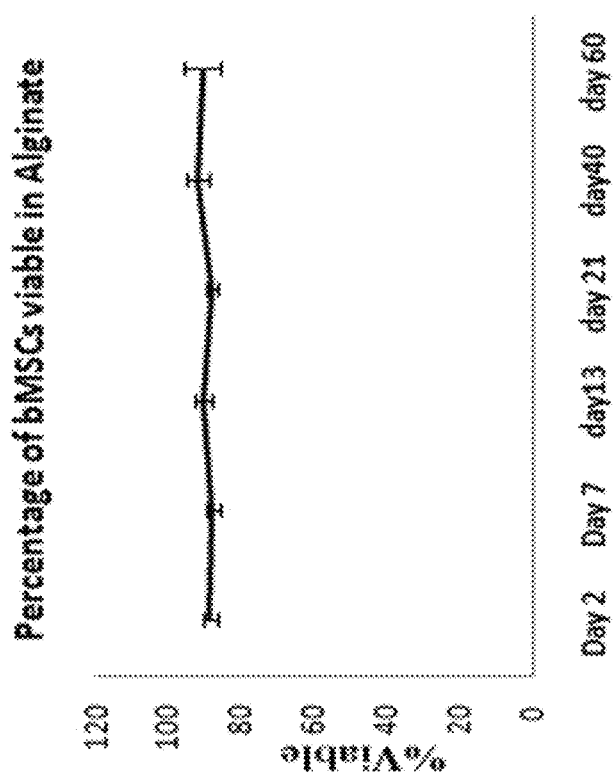

Proliferation rates in different alginate concentrations were also evaluated. Depending on the concentration of the alginate micro-environment the MSC proliferation varied. MSCs encapsulated in alginate concentrations of 2.5 and 1.7% did not support MSC proliferation. However, 2.2% resulted in significant proliferation of MSCs over time. This proliferation reached a plateau phase after 21 days in culture, where the final concentration per capsule was twice the initial seeding density (FIG. 16C).

Proliferation was assessed post encapsulation as previously described. Briefly, alginate capsules were dissociated via Na citrate for 1 hour, at which point cells are freely floating in solution. Sample from this solution was stained with trypan blue and counted to assess the number of cells in the solution. The cell count was then normalized to the number of capsules in the initial solution.

Example 19

Immunocytochemistry

Capsules representing day 2, 7, 14, and 21 days of culture were fixed using 4% paraformaldehyde for 15 minutes and stained for MSC specific surface markers CD200, CD105, CD73. All cells were compared to isotype controls and evaluated for percent positive and relative intensities Example 20

Differentiation Assays

Capsules at a cell seeding density of 5 million cells/ml were cultured for at least 21 days. Medium was changed every three days and on days 2, 7, 14, and 21, 1500 capsules were fixed in formalin for 15 minutes and stored at 4 degrees until analysis was performed. Cells were stained for surface markers CD105, CD200 and CD90 on each day. Capsules were washed three times for ten minutes in PBS then blocked with 10% goat serum for 30 minutes. Before capsules were incubated with antibody they were washed for 30 minutes with PBS. Capsules were incubated with primary antibody over night at 4 degrees. The capsules were washed for 30 minutes with PBS and then incubated with secondary antibody for 45 minutes at room temperature. Capsules where washed for 30 minutes with PBS stained with DAPI and analyzed via spinning disk confocal microscopy. 15 Z sections of each capsule were taken to create projection images of all the cells in the capsule. The cells were analyzed for percent positive as well as the signal intensity of the protein over time.

On day 21 capsules were fixed to perform staining for adipocyte, osteoblast and chondrocyte differentiation.

Oil red-O staining was employed to measure adipocyte differentiation. Von Kossa staining was performed to measure osteoblast differentiation and Alcian blue staining was utilized to assess cartilage differentiation.

Figure 17:
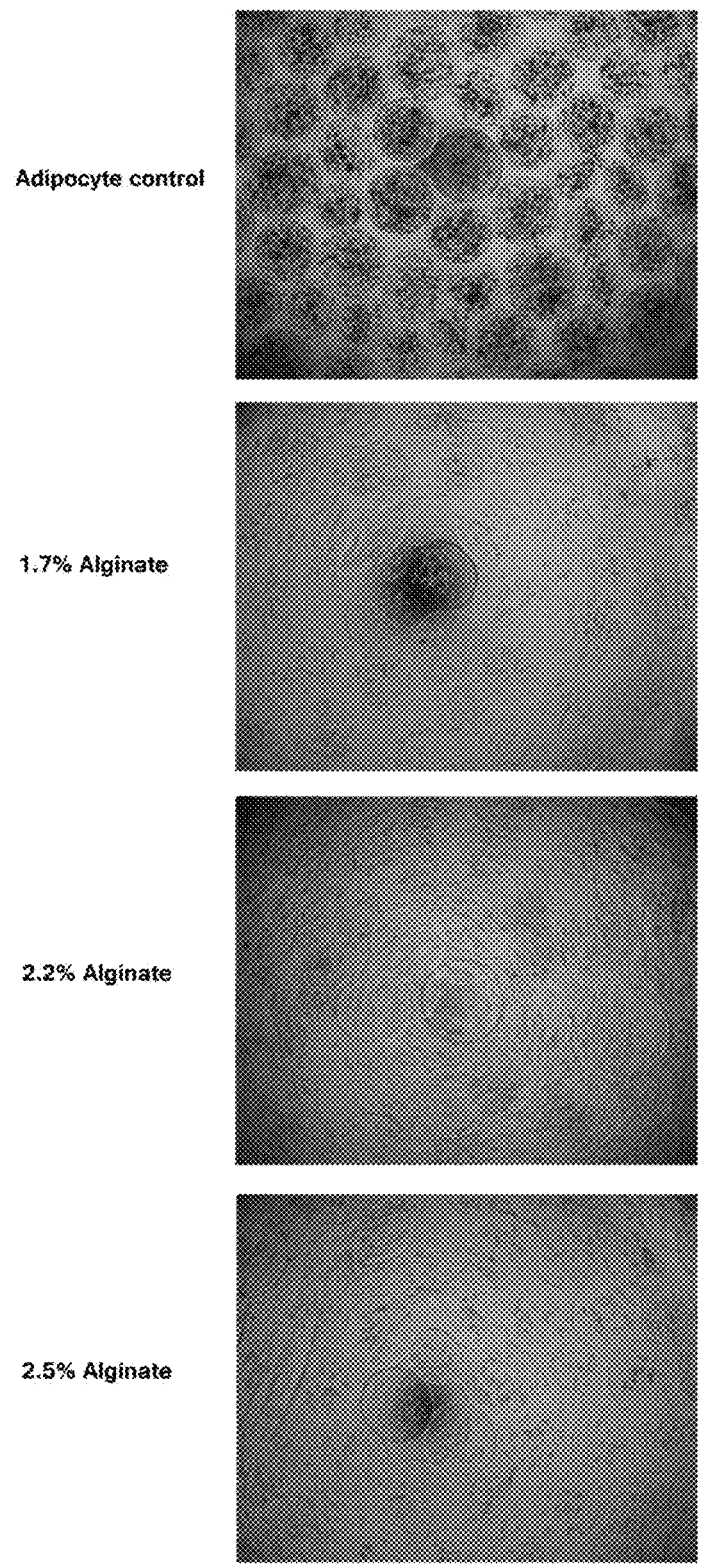
FIG. 17 illustrates the results of assessment of MSC differentiation in the capsule microenvironment. On day 2 post encapsulation, capsules did not stain positive for any differentiation marker. On day 21 of culture capsules did not stain positive for adipocyte or osteocyte differentiation. On day 21, depending on what alginate concentration was used, the experiment did result in chondrocyte differentiation.
Figure 18A:
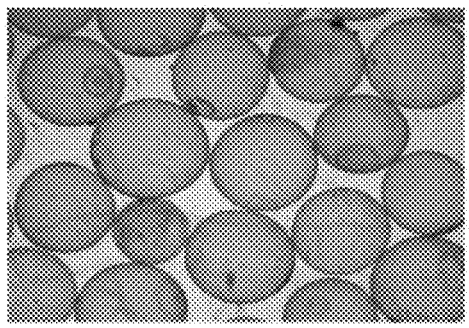
FIGS. 18A, 18B, 18C, 18D, 18E, 18F, 18G, 18H and 18I illustrate the results of alcian blue staining. (1) 1.7% alginate facilitates spontaneous differentiation of hMSC 21 days post encapsulation. (2) 2.2% and 2.5% concentration of alginate do not support spontaneous differentiation. (3) 2 months post encapsulation, 2.2% and 2.5% alginate can maintain MSCs in an immature phenotype.
Figure 18B:
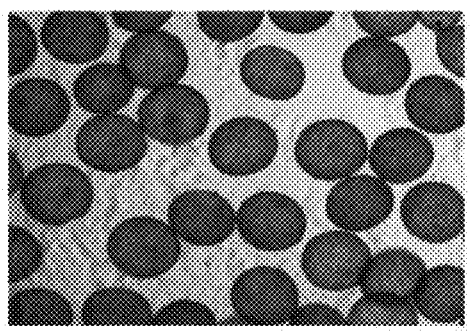
Figure 18C:
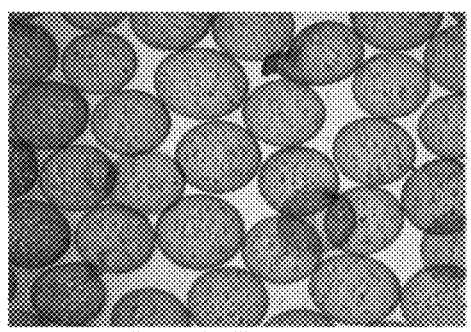
Figure 18D:
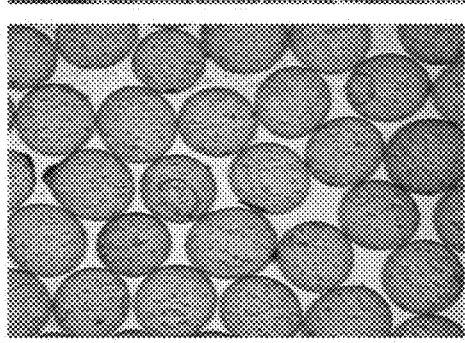
Figure 18E:
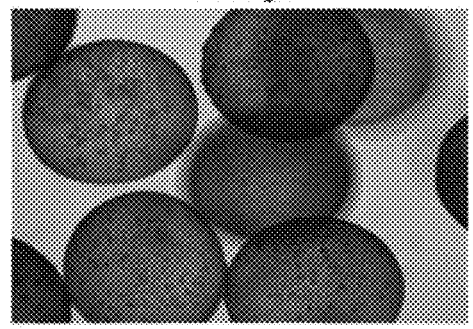
Figure 18F:
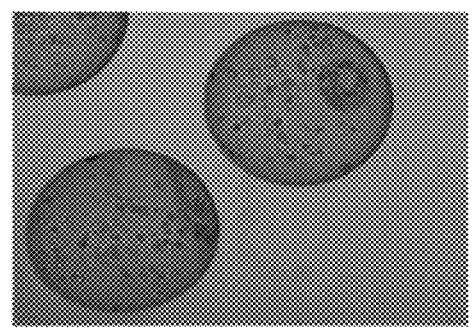
Figure 18G:
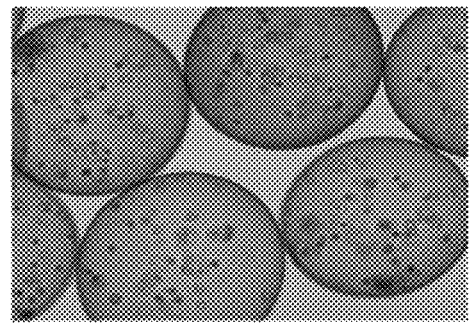
Figure 18H:
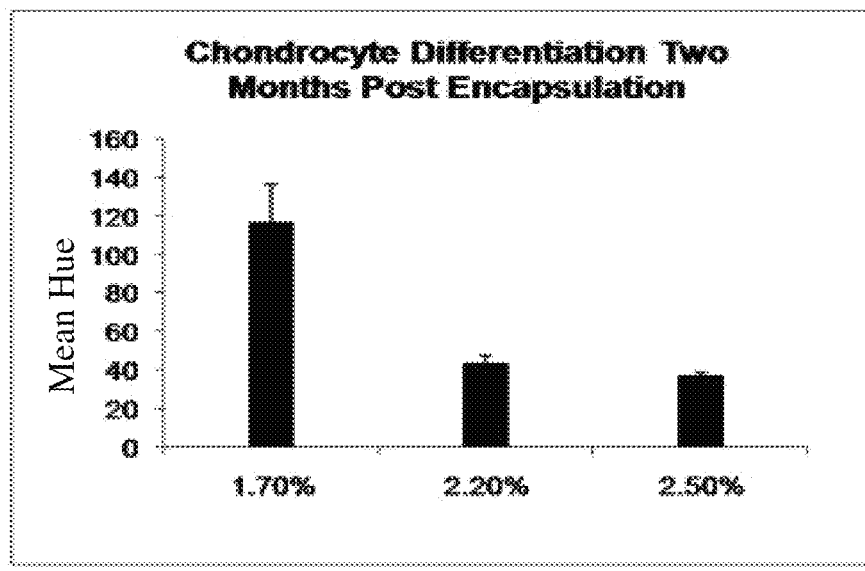
Figure 18I:
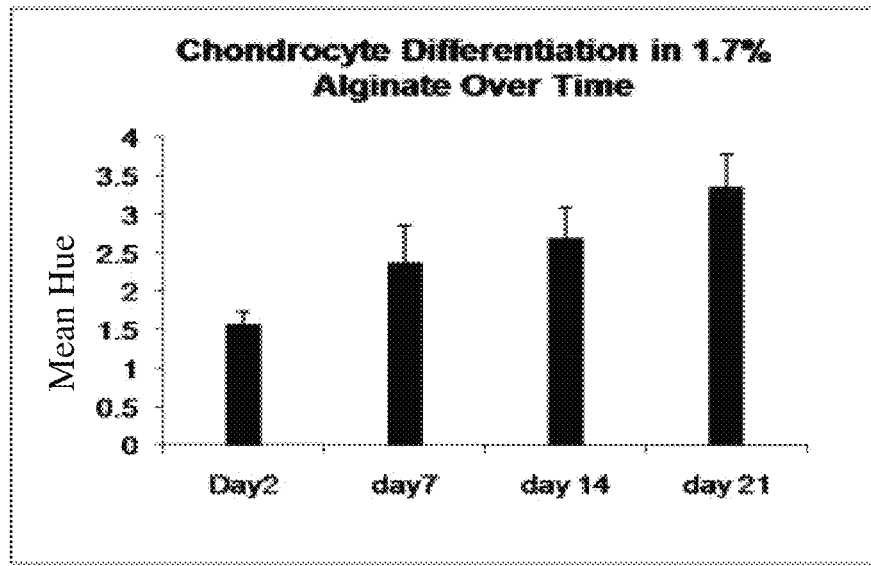
Figure 19A:
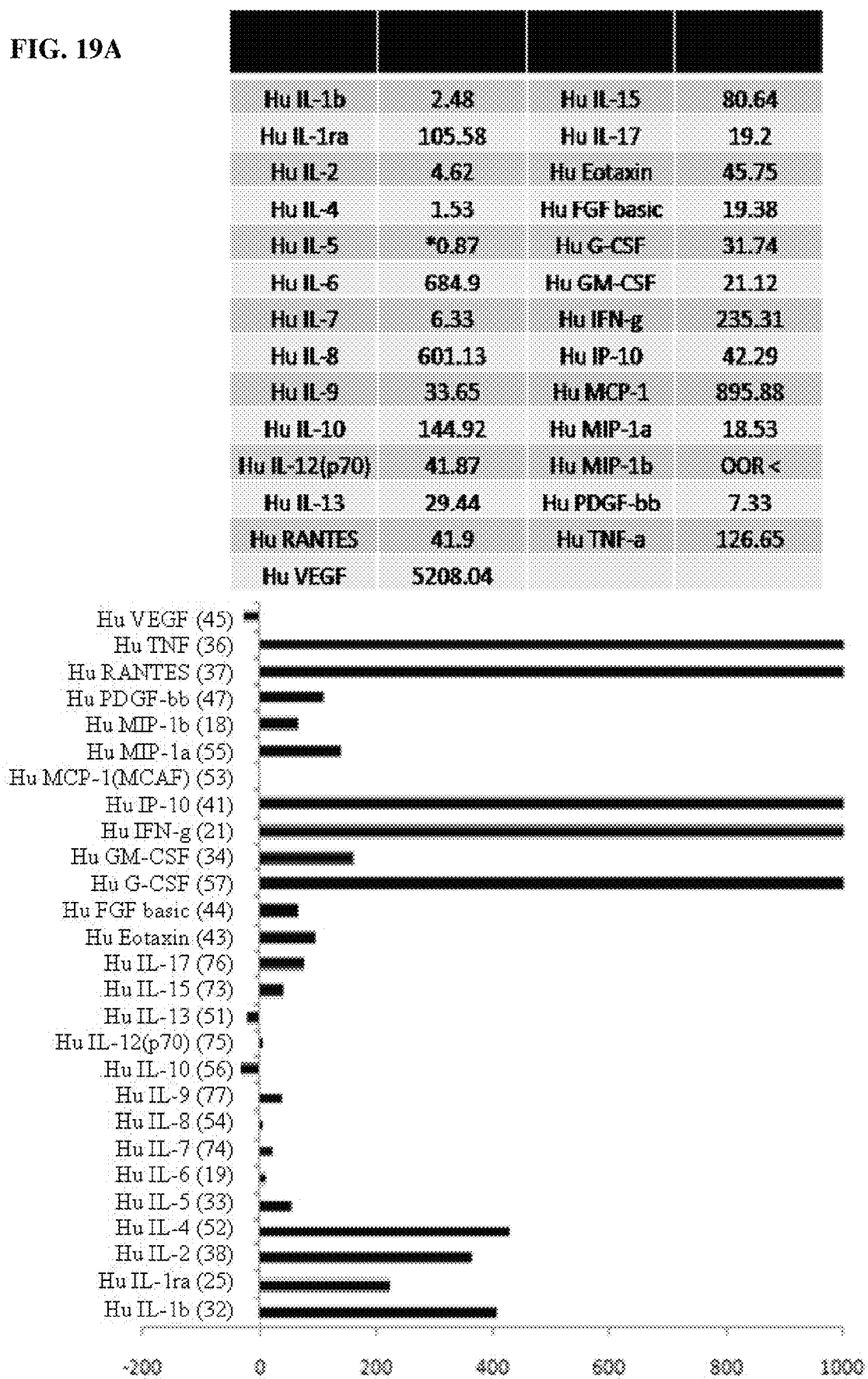
FIGS. 19A and 19B illustrates the secretome from MSCs in monolayer cultures. The table shows the results of constitutive secretion, and the graph shows the results of TNF-α/IFN-γ induced secretion. The figure depicts MSCs secretion of growth factors involved in immuno-regulation and neuron-protection. In the presence of pro-inflammatory factors MSCs can be induced to secrete these factors at a greater rate.
Figure 19B:
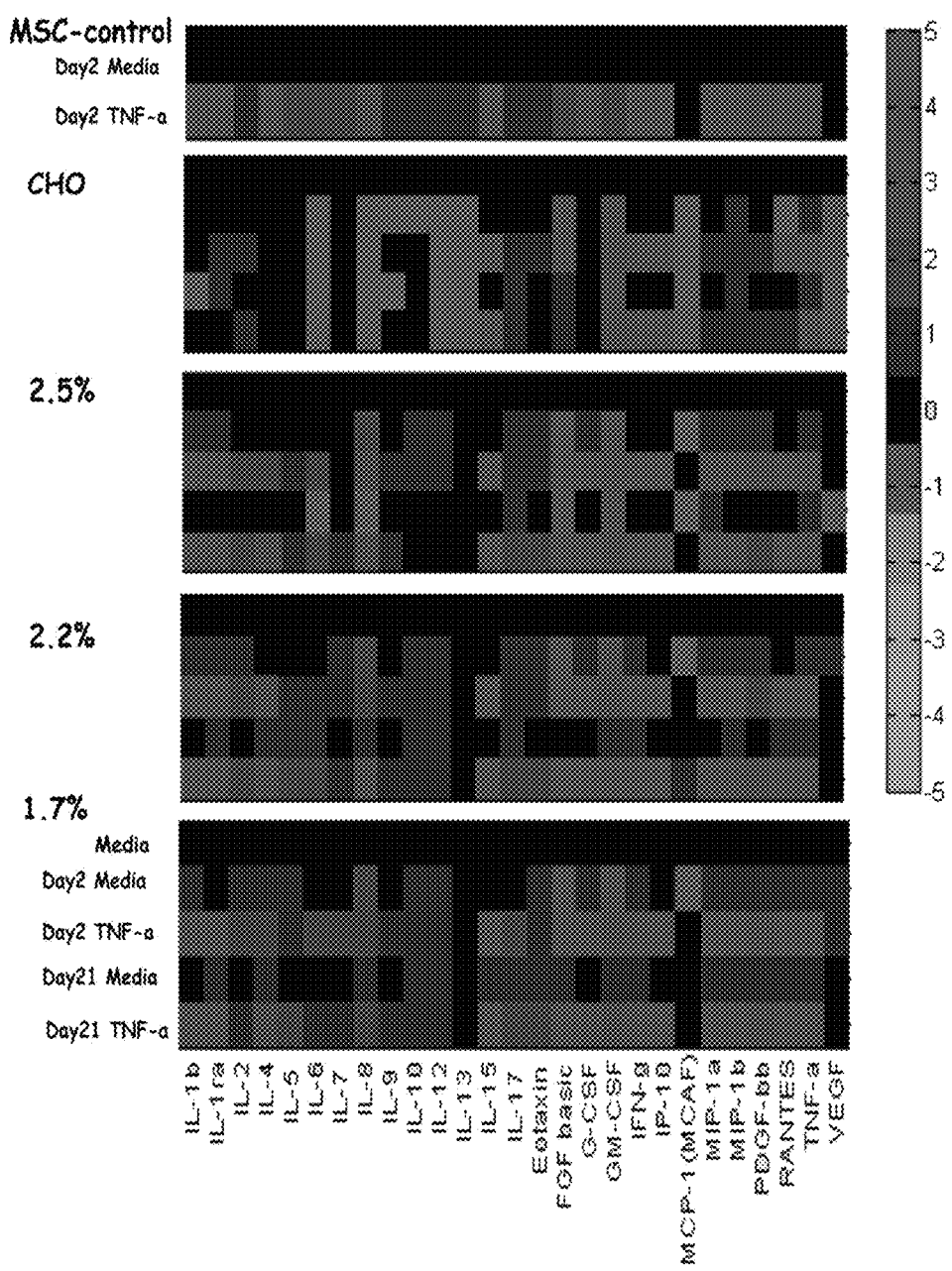

MSCs in their immature phenotype have shown to provide therapeutic benefit in several models of trauma. Therefore, it becomes vital that the capsule microenvironment maintain this immature phenotype. To evaluate the effect of encapsulation on MSC maturation, MSCs were assessed for chondrocytic, adipocytic and osteoblastic markers. On day 21 post-encapsulation, Oil red O staining revealed no spontaneous differentiation into adipocytes in any alginate concentration (FIG. 17). Likewise, fast blue staining for alkaline phosphotase, a marker for osteoblast differentiation, was negative in all conditions (Data not shown). However, alcian blue staining, which detects proteoglycan deposition and hence chondrocyte differentiation, was positive in cells encapsulated in 1.7% alginate by day 21(FIG. 19B). Staining was negative in concentrations of 2.2% and 2.5% at the same time point (FIG. 19C, D). Subsequently, the long-term effects of the capsule micro-environment on MSC phenotype were evaluated. The results indicated that 2 months post encapsulation there was no spontaneous differentiation of MSCs into chondrocytes with capsules at 2.2% and 2.5% (FIG. 19F, G). FIG. 19 indicated that chondrogensis is elevated 1 week post encapsulation and reaches a plateau phase at 21 days (FIG. 19I). All alcian blue conditions were compared to empty capsules in order to determine threshold levels for positive proteoglycan deposition. Therefore, while most alginate conditions did not support MSC differentiation, 1.7% was conducive for chondrocyte differentiation.

Example 21

Assessment of Anti-Inflammatory Function In Vitro-Macrophage Co-Cultures

Figure 20A:
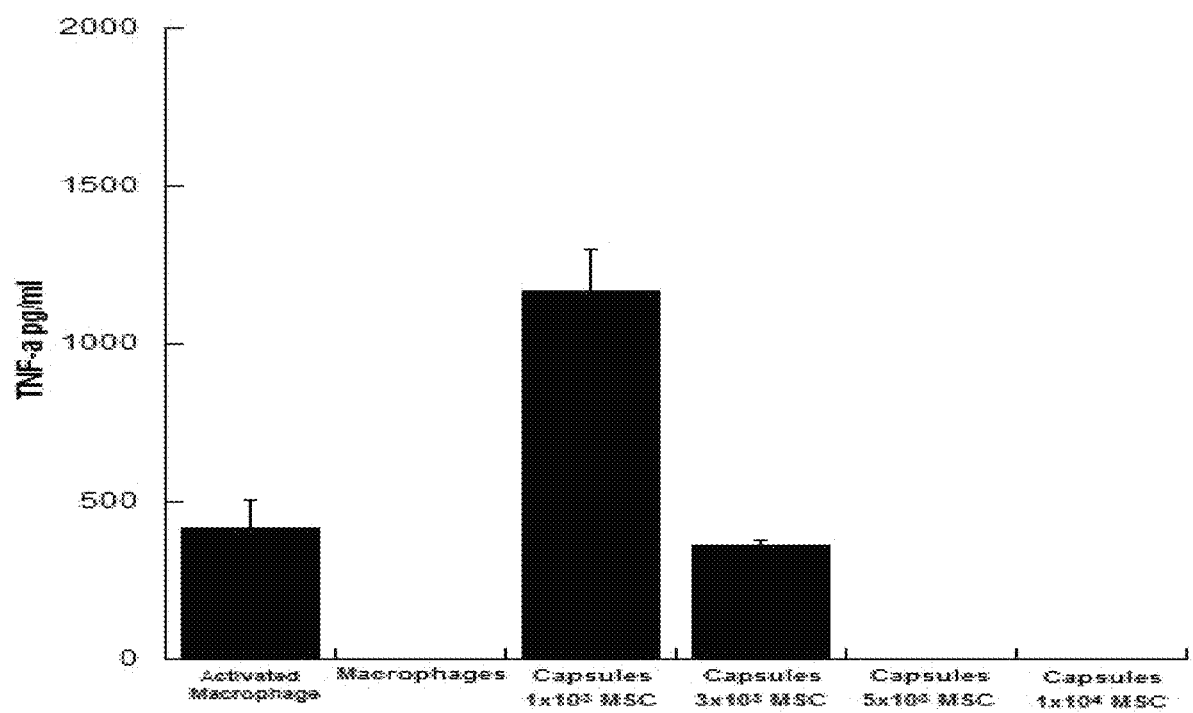
FIG. 20A an 20B illustrate encapsulated MSCs attenuate macrophage pro-inflammatory phenotype.
Figure 20A:
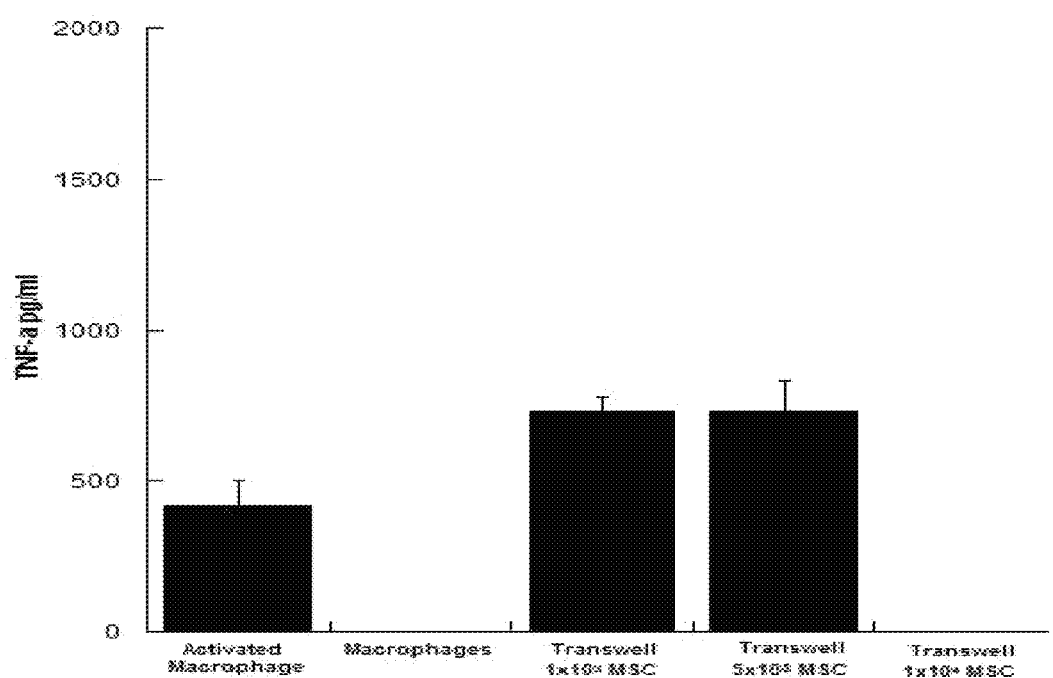

To further establish that encapsulated MSCs could potentially provide tissue protective effects in vivo, a co-culture system was explored using the THP-1 monocyte cell line. Upon LPS stimulation monocytes enter an activation state which corresponds to a pro-inflammatory phenotype. The activated macrophages were cultured in the presence of both encapsulated and freely migrating MSCs. The data indicate that freely migrating MSCs could mitigate the inflammatory macrophage behavior at a critical MSC to macrophage ratio (FIG. 20A). The encapsulated MSC conditions had comparable reduction in TNF-α secretion (FIG. 20A). However, this was achieved with half the number of MSCs as compared to free MSC conditions.

Figure 20B:
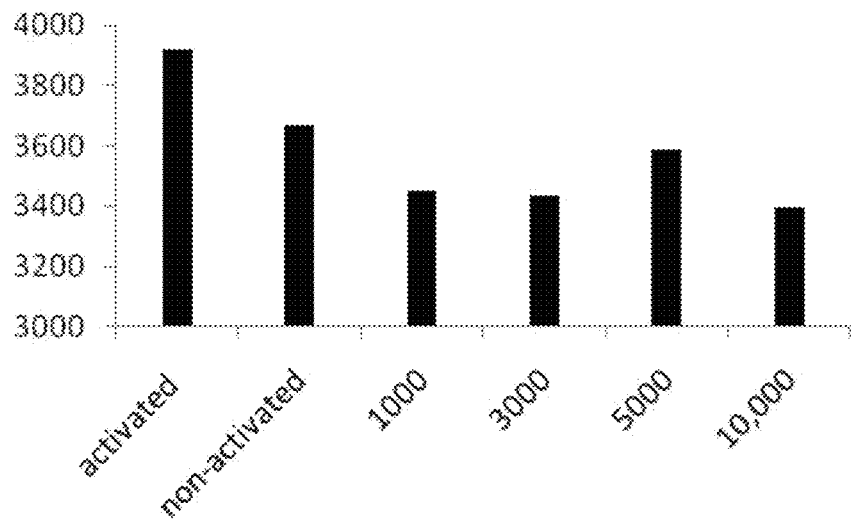
Figure 20B:
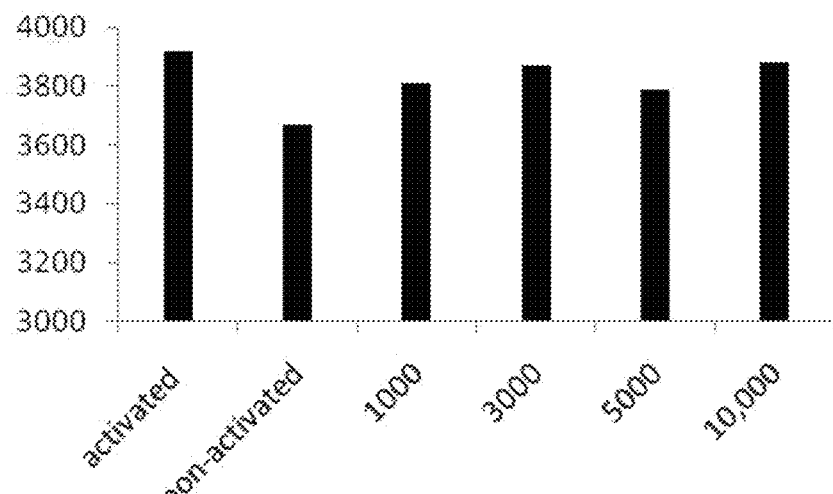
Figure 21A:
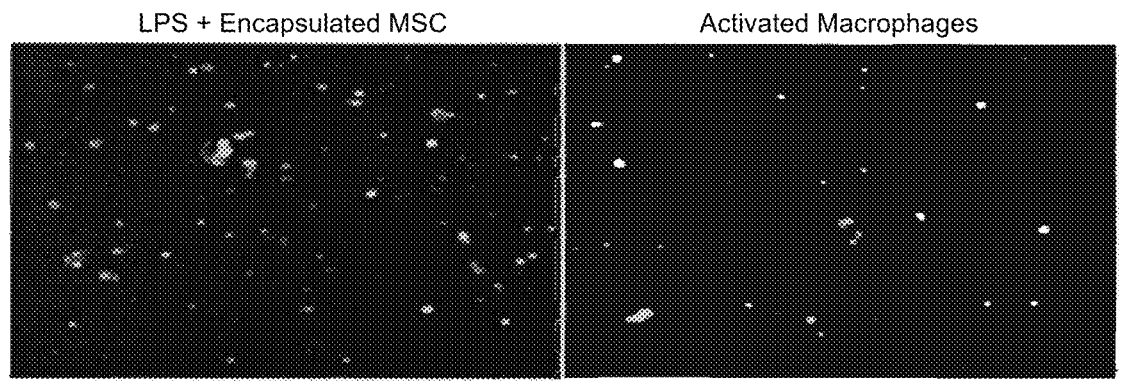
FIGS. 21A and 21B illustrate INOS levels in macrophage co-cultures, and (B) the results of CD206 expression in macrophage/MSC co-cultures.

To further validate the ability of MSCs to mitigate the inflammatory behavior of macrophages, THP-1 cells were analyzed for expression of the activation markers, IBA-1 and iNOS. The expression of surface CD206 (expressed on non-inflammatory M2 macrophages) and secretion of the anti-inflammatory mediator, IL-10, were assessed. Immunofluorescence results indicate that while both transwell and encapsulated MSCs mitigated the IBA-1 expression of activated macrophages, encapsulated MSCs were able to reduce expression to a greater extent (FIG. 20B). In addition, the activated macrophage population expressed high iNOS levels homogenously throughout the population (FIG. 21A). In contrast, evaluation of the iNOS expression levels post encapsulated MSC incubation revealed a differential expression in the macrophage population, with a portion of the macrophage population demonstrating high iNOS levels and the rest, low iNOS levels (FIG. 21A).

Figure 21B:
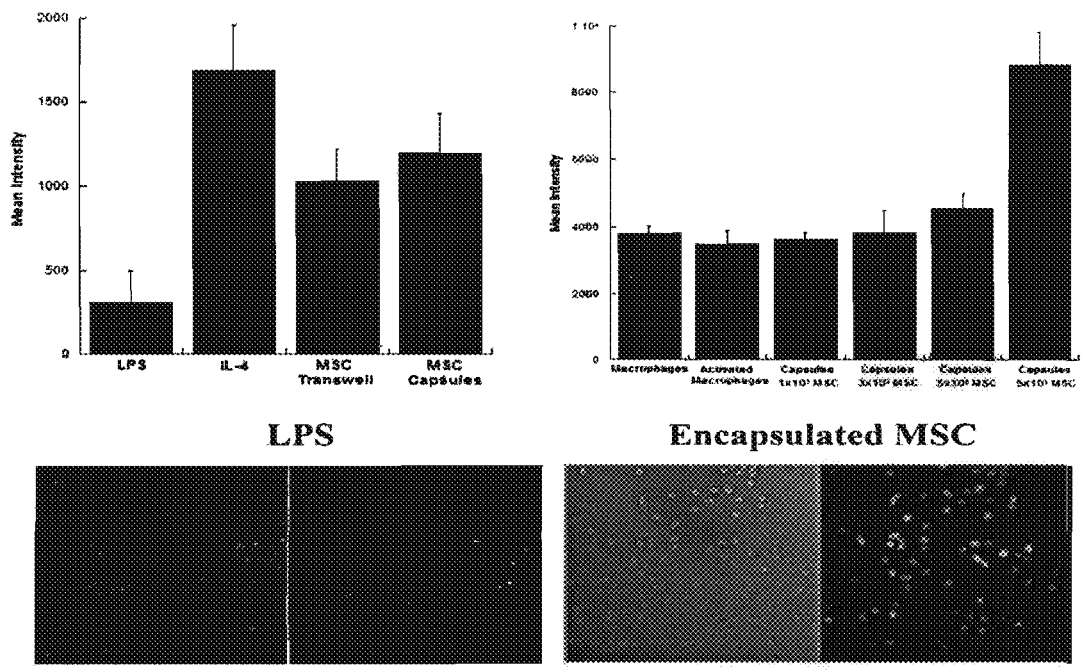
Figure 22A:
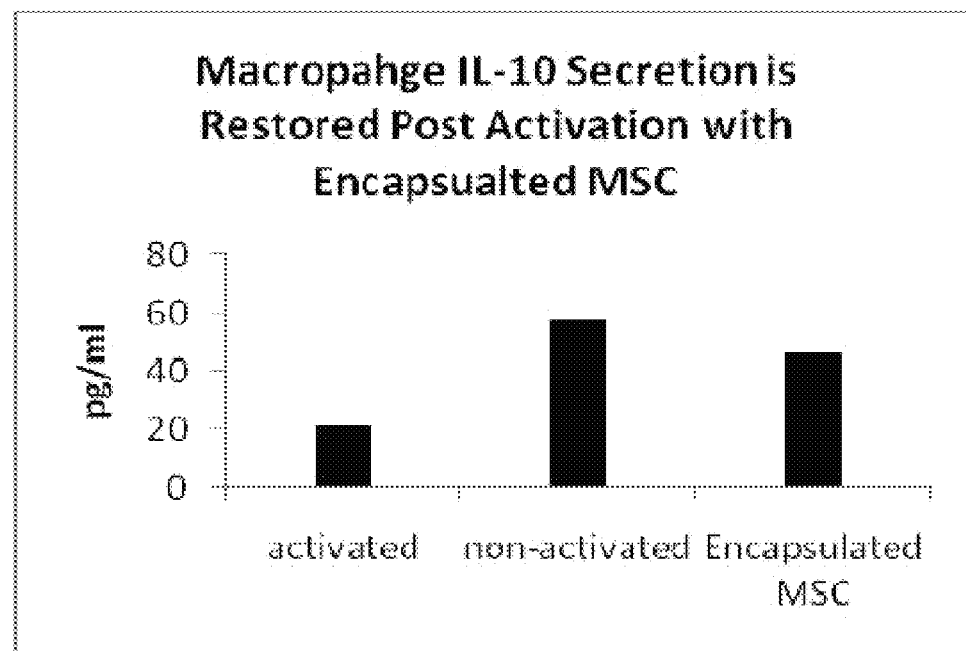
FIGS. 22A and 22B illustrate (FIG. 22A) restored macrophage IL-10 secretion post activation with encapsulated MSCs, and (FIG. 22B) multiplex protein of analysis of several M1 cytokines and growth factors, specifically macrophages, activated macrophages, and encapsulated MSC co-cultures.
Figure 22B:
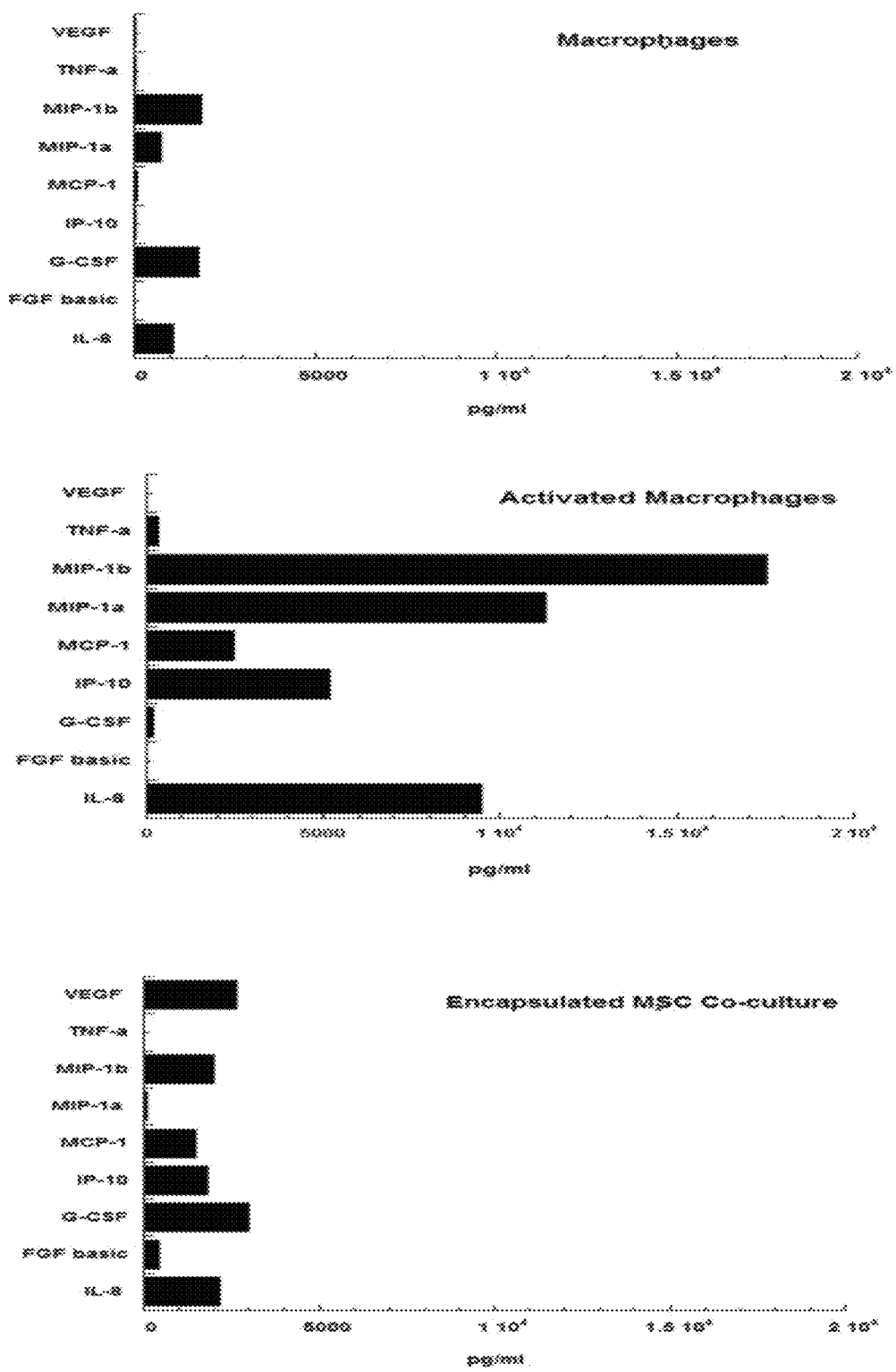

The expression of CD206, a surface protein expressed on tissue protective M2 macrophages, was measured to determine if MSCs effected macrophage population diversion to an M2 phenotype. The analyses indicated that MSC co-culture resulted in elevated levels of CD206 expression (FIG. 21B). Furthermore, the CD206 expression was regulated in a dose dependent manner (FIG. 21B). Next, the IL-10 secretion levels were evaluated, since secretion of this anti-inflammatory cytokine is known to be increased in anti-inflammatory M2 macrophages. The results indicated that, while activation initially reduced IL-10 secretion, IL-10 levels were restored to normal levels when encapsulated MSCs were present during the activation (FIG. 22A). Finally, multiplex protein analyses were utilized to evaluate the effect of encapsulated MSCs on macrophage protein secretion patterns. In the presence of MSCs, inflammatory protein secretion was comparable to non-activated conditions (FIG. 22B). Furthermore, elevation of several growth factors was apparent. These factors are known to play integral roles in cellular proliferation and tissue remodeling (VEGF, G-CSF and bFGF) (FIG. 22B).

Example 22

Cytokine Measurement

Evaluation of cytokine secretion was performed on days 2, 7, 14, and 21. Capsules were placed in 75 um inserts within a 12 well plate and allowed to culture for 48 hours in basal medium. Supernatants were collected and stored at −20 degrees. Analytes were analyzed via multiplex bead analysis for 27 different growth factors Example 23

Secretion Induction

Encapsulated MSCs were induced using the pro-inflammatory cytokines IL-6, TNF-a and IFN-gamma and IL-10 secretion was assessed using ELISA.

MSCs secrete several different factors, many of which have been found to play a role in their immuno-modulatory and tissue protective effects. To evaluate whether the capsule microenvironment can sustain this function, a multiplex assay was run for 27 different factors. In monolayer cultures MSCs secrete several different factors constitutively (FIG. 19A). Among these factors are many cytokines that play critical roles in the inflammatory process, as well as factors responsible for growth and development. Furthermore, in the presence of inflammatory cues, MSCs can be stimulated to secrete these factors at increased rates (FIG. 19A). Our results indicate that relative to monolayer cultures, encapsulated MSCs secrete these factors at comparable levels.

A distinct characteristic of MSCs is that upon stimulation, their secretion patterns are increased (FIG. 19A) presumably to assist in controlling the effects of tissue pathology. To determine the ability of the capsule environment to sustain this behavior, MSCs were cultured in the presence of TNF-α and IFN-γ. The secretion patterns were observed to be elevated compared to monolayer cultures (FIG. 19B). Furthermore, the induction was observed over time and found to be sustained for the 21 day culture period.

Example 24

Immuno-Therapeutics of MSCs

MSCs were tested in acute organ failure, using a model of fulmanant liver failure. Treatment with concentrated MSC supernatant (CM) 24 hours post injury induction, showed a decrease in periportal immune cell infiltration with edema and fibrin deposition, characteristic of tissue repair (FIG. 24(A-D)). In addition, analysis of serum cytokine levels revealed statistically significant difference in inflammatory and anti-inflammatory cytokine expression after MSC-CM treatment (Parekkadan, B., et al., *PLoS ONE*, 2, e941 (2007)). Examination of MSC conditioned medium using a high-density cytokine array revealed a number of molecules involved in immuno-regulation, inflammation, hematopoiesis, proliferation and activation of immune-cells with a large fraction that can be broadly clustered as growth factors (37%), chemokines (30%) and cytokines (19%). We found that MSCs secreted anti-inflammatory molecules and neurogenic soluble factors including BDNF and GDNF.

Example 25

Transplantation of MSCs into the Contused Spinal Cord

Figure 25:
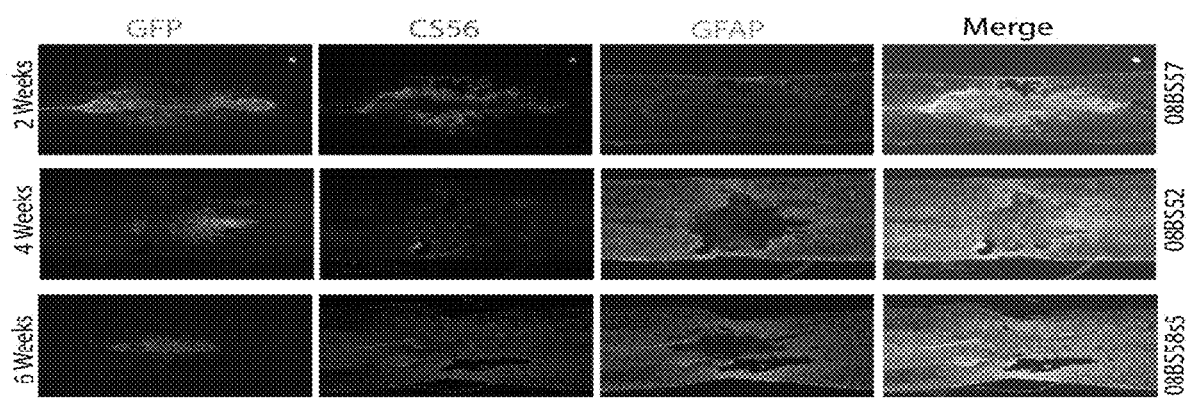
FIG. 25 illustrates an experiment in which GFP+ rat MSCs (2×106) were injected intraspinally into Fisher rats at the injury site immediately after spinal cord contusion (12.5 mm weight drop with MASCIS Impactor). Two-six weeks later the rats were anesthesized, perfusion fixed with 4% paraformaldehyde and saggital sections were immunostained after cryosectioning for chondrotin sulfate proteoglycans (CS56) and GFAP; panels on the right show merged images including the GFP fluorescence of the transplanted rat MSCs. Note the complementary patterns of GFP with CS56, and reduced GFAP signals adjacent to regions of the GFP+ MSCs.

We have isolated rat MSCs from bone marrow of GFP-expressing rats and injected them into spinal cords following contusion with the MASCIS impactor (Basso, D. M., et al., *J. Neurotrauma*, 13, 343-359 (1996)). Histological analysis 2-6 weeks after injury and transplant revealed that MSCs remained in the injury site (FIG. 25), CSPGs were excluded from regions occupied by the MSCs and levels of GFAP were lower in regions of tissue that are occupied or adjacent to the MSCs. The results suggest that MSCs locally suppress expression of CSPG and gliosis. Similarly, the CSPG NG2 was excluded from the injury site where MSCs were located. There was reduced accumulation of ED1+ cells in the injury site particularly where the GFP+ MSCs accumulated, suggesting local immuno-suppression by the rat MSCs.

Example 26

Transplantation of MSCs into the Contused Spinal Cord Via LP

Figure 26:
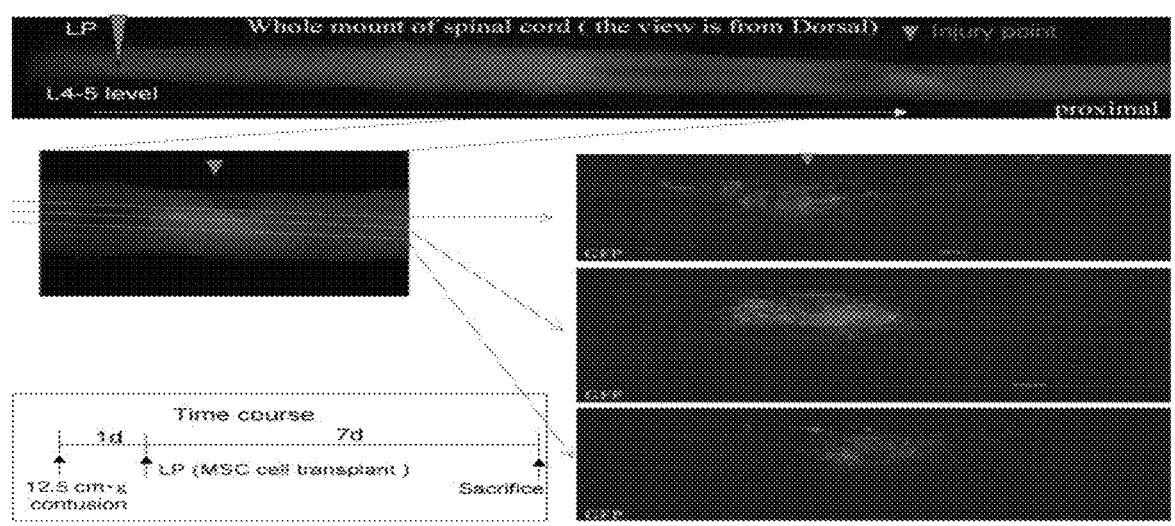
FIG. 26 illustrates an experiment in which GFP+ rat MSCs (2×106) were injected via LP into Fisher rat 1 day after spinal cord contusion (12.5 mm weight drop with MASCIS Impactor). One week later the rat was anesthesized, perfusion fixed with 4% paraformaldehyde and a whole mount image was taken (top, enlargement of the injury site in shown on the left). The experimental plan is summarized in the lower left. The right panels show three saggital sections after cryosectioning. Note the dramatic accumulation the GFP+ MSCs in the injury site.

Considering recent success in delivering MSCs to the spinal cord by a less invasive procedure by injection into the lumbar enlargement (Bakshi, et al., *J. Neurotrauma*, 23, 55-65 (2006), Paul, C., et al., *Spine*, 34, 328-334 (2009)), we have delivered rat GFP+ MSCs into the spinal cord one day following contusion with the MASCIS impactor (Basso, et al., 1996). Few if any GFP+ cells remained at the site of injection (LP) at L4-5, whereas GFP+ cells accumulated at the injury site within 1 week of implantation. (FIG. 26). Analysis of serial sagittal sections indicated a wide distribution of the GFP+ MSCs in the injury site, confirming their ability to rapidly home to it. The combined results indicate that MSCs can survive for at least 6 weeks after implantation into the injured spinal cord, they can rapidly home to the injury site from a delivery site several cm away, and they modulate various parameters consistent with the hypothesis that MSCs can suppress immune signaling acutely in the contused spinal cord. This data provides a strong foundation for the experiments in this proposal to further explore MSC function in the contused spinal cord.

Example 27

Injection of Alginate Alone or Containing Human MSCs into SCI Animals

Figure 27:
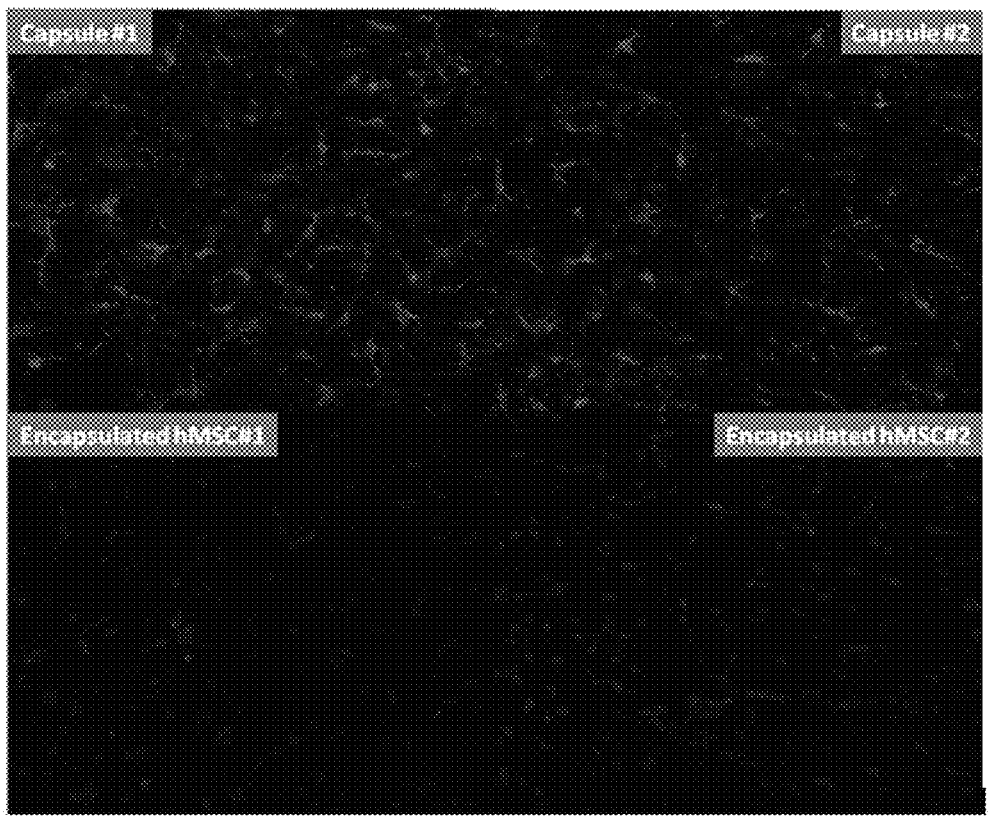
FIG. 27 illustrates an experiment in which encapsulated human MSCs or capsules alone were injected via LP into Sprague Dawley rats 1 day after spinal cord contusion (12.5 mm weight drop with MASCIS Impactor). One week later rats were anesthesized, perfusion fixed with 4% paraformaldehyde and cryosectioned. Cross sections of the spinal cord were immunostained with IBA-1 (red), which recognizes activated microglia. Note that in the dorsal horn 6 mm caudal from the injury epicenter the robust expression of IBA-1 with the capsules alones that typically followed SCI, whereas IBA-1 expression was suppressed dramatically when encapsulated hMSC were injected in two rats for each treatment.

To demonstrate feasibility of alginate introduction, 2,500 capsules (~100 μm diameter) injected by LP into SCI animals had no adverse effects after one week (data not shown). When capsules containing human MSCs were injected into the *cauda equina*, the reactivity for IBA-1 in the vicinity of the spinal cord contusion site was diminished by comparison to capsule alone controls. For example, 6 mm caudal to the injury epicenter there was little IBA-1 immunostaining in rats treated with capsules containing human MSCs by comparison to those treated with capsules alone. (FIG. 27). The results indicate that even when injected at a distance of several cm from the SCI site, encapsulated human MSCs can have effects on inflammatory response in the injury site within a week after delivery.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention, which is defined by the following claims.

What is claimed is:

1. A method for inducing differentiation of stem cells into oligodendrocytes, consisting of: (a) encapsulating the stem cells within a three-dimensional (3D) alginate polyelectrolyte microenvironment; (b) culturing the encapsulated stem cells in a differentiation cell media; (c) supplementing the differentiation cell media with a PPAR δ agonist on any day of from Day 8 to Day 22; and (d) allowing the encapsulated stem cells to differentiate into the oligodendrocytes optionally in the presence of an inducer capable of inhibiting cell aggregation, whereby the resulting differentiated cells comprise more than 80% myelin basic protein (MBP) positive cells.

2. The method of claim 1, wherein said encapsulating comprises: (i) dissolving an alginic acid salt in a medium to form an alginate solution; (ii) optionally filtering the alginate solution through a filter; (iii) adding to the alginate solution an aliquot of stem cell suspension to form a cell-alginate mixture; (iv) generating alginate beads using an electrostatic bead generator; (v) allowing the alginate beads to polymerize; and (vi) suspending the beads in a solution comprising a polyelectrolyte.

3. The method of claim 2, wherein said culturing comprises: (i) removing the polyelectrolyte solution; (ii) washing the beads; (iii) suspending the washed beads in a differentiation media, wherein said differentiation media optionally comprises an inducer; and (iv) optionally replacing the differentiation media periodically.

4. The method of claim 3, wherein said polyelectrolyte is poly-L-lysine, and said inducer is retinoic acid.

5. The method of claim 1, wherein the stem cells are embryonic stem cells (ES cells).

6. The method of claim 5, wherein the inducer is retinoic acid (RA).

7. The method of claim 1, wherein the PPAR δ agonist is GW0742.

8. The method of claim 1, wherein the inducer is an E-Cadherin antibody.

9. The method of claim 1, wherein steps (a), (b), (c), and (d) are performed in the absence of a growth factor.

10. The method of claim 1, wherein the PPAR δ agonist is supplemented on any day of from Day 8 to Day 16.

11. The method of claim 1, wherein the PPAR δ agonist is supplemented on any day of from Day 8 to Day 12.

* * * * *